(12) United States Patent
Rands et al.

(10) Patent No.: US 12,318,477 B2
(45) Date of Patent: *Jun. 3, 2025

(54) INJECTABLE AND INHALABLE FORMULATIONS

(71) Applicant: CYBIN UK LTD, London (GB)

(72) Inventors: Peter Rands, London (GB); Carol Routledge, London (GB); Marie Layzell, London (GB); Ellen James, London (GB); Zelah Joel, London (GB); Tiffanie Benway, London (GB); Meghan Good, London (GB)

(73) Assignee: Cybin UK Ltd, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/056,771

(22) Filed: Nov. 18, 2022

(65) Prior Publication Data

US 2023/0149293 A1     May 18, 2023

(30) Foreign Application Priority Data

Nov. 18, 2021 (TW) ................................. 110143066
Nov. 18, 2021 (WO) ................. PCT/EP2021/082227
Dec. 24, 2021 (GB) ...................................... 2119021
Mar. 2, 2022 (WO) ................. PCT/EP2022/055324

(51) Int. Cl.
| A61K 9/00 | (2006.01) |
| A61K 9/19 | (2006.01) |
| A61K 31/4045 | (2006.01) |
| A61K 45/06 | (2006.01) |

(52) U.S. Cl.
CPC .............. *A61K 9/0019* (2013.01); *A61K 9/19* (2013.01); *A61K 31/4045* (2013.01); *A61K 45/06* (2013.01)

(58) Field of Classification Search
CPC ..... A61K 9/0019; A61K 9/19; A61K 31/4045
See application file for complete search history.

(56) References Cited

U.S. PATENT DOCUMENTS

| 4,336,378 | A | 6/1982 | Brand et al. |
| 8,268,856 | B2 | 9/2012 | Hamann et al. |
| 11,000,534 | B1 | 5/2021 | Sippy |
| 11,242,318 | B2 | 2/2022 | Nivorozhkin et al. |
| 11,406,619 | B2 | 8/2022 | Layzell et al. |
| 11,578,039 | B2 | 2/2023 | Rands et al. |
| 11,643,390 | B2 | 5/2023 | Rands et al. |
| 11,660,289 | B2 | 5/2023 | Rands et al. |
| 11,697,638 | B2 | 7/2023 | Rands et al. |
| 11,773,062 | B2 | 10/2023 | Rands et al. |
| 2002/0022667 | A1 | 2/2002 | Pace et al. |
| 2009/0076121 | A1 | 3/2009 | Czarnik |
| 2013/0129812 | A1 | 5/2013 | Ozpolat et al. |
| 2018/0221396 | A1 | 8/2018 | Chadeayne |
| 2020/0339519 | A1* | 10/2020 | Kim ..................... C07D 239/42 |
| 2020/0390746 | A1 | 12/2020 | Rands et al. |
| 2020/0397752 | A1 | 12/2020 | Perez Castillo et al. |
| 2021/0378969 | A1 | 12/2021 | Rands et al. |
| 2021/0395201 | A1 | 12/2021 | Rands et al. |
| 2021/0403426 | A1 | 12/2021 | Rands et al. |
| 2022/0024956 | A1 | 1/2022 | Slassi et al. |
| 2022/0062237 | A1 | 3/2022 | Layzell et al. |
| 2022/0081396 | A1 | 3/2022 | Rands et al. |
| 2022/0168275 | A1 | 6/2022 | Rands et al. |
| 2022/0202775 | A1 | 6/2022 | Rands et al. |
| 2023/0086574 | A1 | 3/2023 | Rands et al. |
| 2023/0167056 | A1 | 6/2023 | Rands et al. |
| 2023/0181530 | A1 | 6/2023 | Rands et al. |
| 2023/0250059 | A1 | 8/2023 | Rands et al. |
| 2024/0016782 | A1 | 1/2024 | Rands et al. |
| 2024/0217929 | A1 | 7/2024 | Rands et al. |

(Continued)

FOREIGN PATENT DOCUMENTS

| GB | 2585978 A | 1/2021 |
| GB | 2586940 A | 3/2021 |
| GB | 2596884 A | 1/2022 |

(Continued)

OTHER PUBLICATIONS

Brito-da-Costa et al., Toxicokinetics and Toxicodynamics of Ayahuasca Alkaloid N,N-Dimethyltryptamine (DMT), Harmine, Hamaline and Tetrahydroharmine: Clinical and Forensic Impact, 2020, Pharmaceuticals, 12(334), 1-36, DOI: 10.3390/ph13110334 (Year: 2020).*
Cai, Monamine oxidase inhibitors: Promising therapeutic agents for Alzheimers disease, 2014, Molecular Medicine Reports, 9(5), 1533-1542, DOI:10.3892/mmr.2014.2040 (Year: 2014).*
Hopkins et al., Large-volume IM injections: A review of best practices, https://www.oncologynurseadvisor.com/home/hot-topics/chemotherapy/large-volume-im-injections-a-review-of-best-practices/; accessed Feb. 9, 2023; published Feb. 2013; pp. 32-37 (Year: 2013).*
Barker, et al., "Comparison of the Brain Levels of N N-Dimethyltryptamine and a,a,B,B-Tetradeutero N, N-Dimethyltryptamine Following Intraperitoneal Injection", Biochemical Pharmacology, vol. 31, No. 15, pp. 2513-2516 Jan. 20, 1982 (Year: 1982).*

(Continued)

*Primary Examiner* — Andrew S Rosenthal
(74) *Attorney, Agent, or Firm* — Heslin Rothenberg Farley & Mesiti P.C.

(57) ABSTRACT

The present invention relates to aqueous pharmaceutical formulations, methods for their production, and uses thereof. The aqueous pharmaceutical formulations comprise a salt of an optionally substituted dimethyltryptamine compound and water, with a pH from 5 to 6.5, preferably from about 5 to about 6, and a concentration of the optionally substituted dimethyltryptamine compound of about 10 mg/ml or greater as the freebase equivalent. These formulations can comprise an effective dose of an optionally substituted dimethyltryptamine compound for use in psychedelic assisted therapy within a volume of 5 ml or less. Such formulations are surprisingly suitable both for intramuscular injection and nebulised inhalation, being both stable and clinically acceptable, and have potential uses in the treatment of psychiatric or neurological disorders.

21 Claims, 3 Drawing Sheets

(56) References Cited

U.S. PATENT DOCUMENTS

2024/0325351 A1 10/2024 Rands et al.

FOREIGN PATENT DOCUMENTS

| WO | 02083144 | A1 | 10/2002 | |
|---|---|---|---|---|
| WO | 2004085392 | A1 | 10/2004 | |
| WO | 2008049116 | A2 | 4/2008 | |
| WO | 2008071455 | A1 | 6/2008 | |
| WO | 2009049030 | A1 | 4/2009 | |
| WO | 2009087682 | A2 | 7/2009 | |
| WO | 2009133455 | A2 | 11/2009 | |
| WO | 2018195455 | A1 | 10/2018 | |
| WO | 2019081764 | A1 | 5/2019 | |
| WO | 2020136466 | A1 | 7/2020 | |
| WO | 2020169850 | A1 | 8/2020 | |
| WO | 2020169851 | A1 | 8/2020 | |
| WO | 2020176597 | A1 | 9/2020 | |
| WO | 2020176599 | A1 | 9/2020 | |
| WO | 2020245133 | A1 | 12/2020 | |
| WO | 2021089872 | A1 | 5/2021 | |
| WO | 2021089873 | A1 | 5/2021 | |
| WO | 2021116503 | A2 | 6/2021 | |
| WO | 2021155470 | A1 | 8/2021 | |
| WO | WO-2021234608 | A1 * | 11/2021 | ......... A61K 31/4045 |
| WO | 2021244831 | A1 | 12/2021 | |
| WO | 2022011350 | A1 | 1/2022 | |
| WO | 2022031566 | A1 | 2/2022 | |
| WO | 2022043227 | A1 | 3/2022 | |
| WO | 2022069690 | A2 | 4/2022 | |
| WO | 2022082058 | A1 | 4/2022 | |
| WO | 2022117359 | A1 | 6/2022 | |
| WO | 2022117640 | A1 | 6/2022 | |

OTHER PUBLICATIONS

Abb "Freeze drying in the pharmaceutical industry" (https://new.abb.com/control-systems/industry-specific-solutions/pharmaceutical-and-life-sciences/freeze-drying-in-the-pharmaceutical-industry; accessed Feb. 9, 2023; archived via WayBack Machine Dec. 31, 2017) (Year: 2017).*

Millrock Technology "What is Lyophilization?" (https://www.millrocktech.com/lyosight/lyobrary/what-is-lyophilization/; accessed Feb. 9, 2023) (Year: 2023).*

Carbonaro et al., Neuropharmacology of N,N-Dimethyltryptamine, 2016, Brain Res Bull, 126, 74-88, DOI: 10.1016/j.brainresbull.2016.04.016. (Year: 2016).*

Brito-da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact" Pharmaceuticals 2020, 13, 334 (Year: 2020)*

Carbonaro et al. "Neuropharmacology of N,N-dimethyltryptamine" Brain Research Bulletin 126 (2016) 74-88 (Year: 2016).*

Barker et al. "Comparison of the Brain Levels of N,Ndimethyltryptamine and a,a,b,b-Tetradeuteron, N-Dimethyltryptamine Following Intraperitoneal Injection" Biochemical Pharmacology, vol. 31. No. 15, pp. 2513-2516, 1982 (Year: 1982).*

Wang "Tolerability of hypertonic injectables" International Journal of Pharmaceutics 490 (2015) 308-315 (Year: 2015).*

Cai "Monoamine oxidase inhibitors: Promising therapeutic agents for Alzheimer's disease (Review)" Mol. Med. Rep. 9, 1533-1541, 2014 (Year: 2014).*

Abb "Freeze drying in the pharmaceutical industry" (https://new.abb.com/ control-systems/industry-specific-solutions/pharmaceutical-and-life-sciences/freeze-drying-in-the-pharmaceutical-industry; Dec. 31, 2017 (Year: 2017).*

Millrock Technology (https://millrocktech.com/lyosigh/lyobrary /what-is-lypphilization) accessed Feb. 9, 2023 (Year: 2023).*

Ambinter Screening Library, CAS Registry No. 1794811-18-9, Order No. Cat. Amb33838664 Mar. 26, 2020.

Aurora Building Blocks 2, CAS Registry No. 1435934-64-7, Order No. Cat A17.921.638. Feb. 27, 2020.

Barker, et al., "Comparison of the Brain Levels of N N-Dimethyltryptamine and a,a,B,B-Tetradeutero N, N-Dimethyltryptamine Following Intraperitoneal Injection", Biochemical Pharmacology, vol. 31, No. 15, pp. 2513-2516 Jan. 20, 1982.

Barker, Steven A., "N, N-Dimethyltryptamine (DMT), an Endogenous Hallucinogen: Past, Present, and Future Research to Determine Its Role and Function", Frontiers in Neuroscience, vol. 12, Article 536, pp. 1-17 Aug. 6, 2018.

Beaton, et al., "A Comparison of the Behavioral Effects of Proteo- and Deutero-N, N-Dimethyltryptamine", Pharmacology, Biochemistry & Behavior, vol. 16, pp. 811-814 Sep. 8, 1982.

Brandt, et al., "Microwave-Accelerated Synthesis of Psychoactive Deuterated N, N-Dialkylated-[a, a, ?, ?-d4]-Tryptamines", Journal of Labelled Compounds and Radiopharmaceuticals, vol. 51, No. 14, pp. 423-429 Nov. 1, 2008.

Brito-Da-Costa et al. "Toxicokinetics and Toxicodynamics of Ayahuasca Alkaloids N, N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.

Cameron, et el., "Effects of N,N-Dimethyltryptamine on Rat Behaviors Relevant to Anxiety and Depression", ACS Chemical Neuroscience, vol. 9, No. 7, pp. 1582-1590 2018.

Celik, et al., "Binding of Serotonin to the Human Serotonin Transporter. Molecular Modeling and Experimental Validation" Journal of the American Chemical Society, vol. 130, No. 12, pp. 3853-3865 Mar. 2008.

Celik, et al., "Supplementary Information to Binding of Serotonin to the Human Serotonin Transporter. Molecular Modeling and Experimental Validation", Journal of the American Chemical Society, 14 pages Mar. 2008.

Chemieliva Pharmaceutical Product, Cas Registry No. 1794756-39-0, "Supplementary Disclosures", Chemieliva Pharmaceutical Product List, Order No. Cat. CC0034145 Jan. 28, 2021.

Chemieliva Pharmaceutical Product, Cas Registry No. 1794811-18-9, "Supplementary Disclosures", Chemieliva Pharmaceutical Product List, Order No. Cat. CC0034141 Jan. 28, 2021.

Dunlap et al., "Identification of Psychoplastogenic N,N-Dimethylaminoisotryptamine (isoDMT) Analogues through Structure—Activity Relationship Studies", Journal of Medicinal Chemistry, vol. 63, pp. 1142-1155 2020.

Dyck, et al., "Effect of Deuterium Substitution on the Disposition of Intraperitoneal Tryptamine", Biochemical Pharmacology, vol. 35, No. 17, pp. 2893-2896 1986.

Gaujac, et al., Investigations into the polymorphic properties of N,N-dimethyltryptamine by X-ray diffraction and differential scanning calorimetry, Microchemical Journal, vol. 110, pp. 146-157 2013.

Ghosal, et al., "Indole Bases of Desmodium Gyrans", Phytochemistry (Elsevier), vol. 11, No. 5, pp. 1863-1864 1972.

Grina, et al., "Old and New Alkaloids From Zanthoxylum Arborescens", Journal of Organic Chemistry, vol. 47, No. 13, pp. 2648-2651 1982.

Halberstadt, et al., "Behavorial effects of α,α,ß,ß-tetradeutero-5-MeO-DMT in rats: comparison with 5-MeO-DMT administered in combination with a monoamine oxidase inhibitor", Psychopharmacology, vol. 221, pp. 709-718. Jan. 6, 2012.

Ibrahim, et al., "Marine inspired 2-(5-Halo-1 H-indol-3-yl)-N,N-dimethylethanamines as Modulators of Serotonin Receptors: An Example Illustrating the Power of Bromine as Part of the Uniquely Marine Chemical Space", Marine drugs, vol. 15, No. (8), pp. 248/1-248/14 2017.

McIlhenny, et al., "Direct Analysis of Psychoactive Tryptamine and Harmala Alkaloids in the Amazonian Botanical Medicine Ayahuasca by Liquid Chromatography-electrospray Ionization-tandem Mass Spectrometry", Journal of Chromatography A, vol. 1216, No. 51, 9 pages 2009.

Morris, et al., "Indolealkylamine Metabolism: Synthesis of Deuterated Indolealkylamines as Metabolic Probes", Journal of Labelled Compounds and Radiopharmaceuticals, John Wiley & Sons Ltd., vol. 33, No. 6, pp. 455-465 1993.

(56) References Cited

OTHER PUBLICATIONS

MuseChem Product List, CAS Registry No. 1794756-39-0, Order No. Cat. R055190. Apr. 21, 2020.
Queiroz, et al., "Chemical Composition of the Bark of Tetrapterys Mucronata and Identification of Acetylcholinesterase Inhibitory Constituents", Journal of Natural Products, vol. 77, No. 3, 2014, pp. 650-656 2014.
Rands et al., Unpublished U.S. Appl. No. 17/469,063, filed Sep. 8, 2021.
Rands et al., Unpublished U.S. Appl. No. 17/574,424, filed Jan. 12, 2022.
Riga, et al., The serotonin hallucinogen 5-MeO-DMT alters cortico-thalamic activity in freely moving mice: Regionally-selective incolovement of 5-HT1A and 5-HT2A receptors, Neuropharmacology, vol. 142, pp. 219-230 2017.
Sard, et al., "SAR of psilocybin analogs: Discovery of a selective 5-HT2c agonist", Bioorganic & Medicinal Chemistry Letters 15, vol. 15, No. 20, pp. 4555-4559 2005.
Servillo, et al., "Citrus Genus Plants Contain N-Methylated Tryptamine Derivatives and Their 5-Hydroxylated Forms", Journal of Agricultural and Food Chemistry, vol. 61, No. 21, pp. 5156-5162 2013.
Strassman et al., "Dose-Response Study of N, N-Dimethyltryptamine in Humans: II. Subjective Effects and Preliminary Results of a New Rating Scale", Archives of General Psychiatry, Chicago, IL, vol. 51(2), pp. 98-108 Feb. 1994.
Tearavarich et al. "Microwave-Accelerated Preparation and Analytical Characterization of 5-ethoxy-N,N-dialkyl-[α,α,ß,ß-H4]- and [α,α,ß,ß-D4]-tryptamines", Drug Testing and Analysis, vol. 3, No. 9, pp. 597-608 Dec. 2010.
Timmins, Expert Opin Ther Pat., 24(10), pp. 1067-1075. Oct. 2014.
Walker, et al., "Gas Chromatographic-Mass Spectrometric Isotope Dilution Assay for N,N-Dimethyltryptamine in Human Plasma", Biochemical Medicine, vol. 8, pp. 105-113 1973.
Pires et al., "Gas Chromatographic Analysis of Dimethyltryptamine and ß-Carboline Alkaloids in Ayahuasca, an Amazonian Psychoactive Plant Beverage", Phytochemical Analysis, vol. 20, pp. 149-153. Jan. 12, 2009.
Silveira et al., "Stability Evaluation of DMT and Harmala Alkaloids in Ayahuasca Tea Samples", Molecules, vol. 25, 11 pages. 2020.
Reiff et al., "Psychedelics and Psychedelic-Assisted Psychotherapy", Am J. Psychiatry, 177:5, pp. 391-410. May 2020.
Roseman et al., "Quality of Acute Psychedelic Experience Predicts Therapeutic Efficacy of Psilocybin for Treatment-Resistant Depression", Frontiers in Pharmacology, vol. 8, Article 974, 10 pages. Jan. 2018.

Atzrodt et al. Deuterium- and Tritium-Labelled Compounds: Applications in the Life Sciences, Angew. Chem. Int. Ed., vol. 57, pp. 1758-1784. 2018.
U.S. Appl. No. 18/252,949 to Rands et al. May 15, 2023.
Rands et al., Unpublished U.S. Appl. No. 18/711,130, filed May 17, 2024.
Andersen et al., "Therapeutic Effects of Classic Serotonergic Psychedelics: A Systematic Review of Modern-Era Clinical Studies", Acta Psychiatrica Scandinavica, vol. 143, pp. 101-118. 2021.
Barker, "Administration of N,N-dimethyltryptamine (DMT) in Psychedelic Therapeutics and Research and the Study of Endogenous DMT", Psychopharmacology, vol. 239, pp. 1749-1763. 2022.
Avis, "Chapter 84: Parental Preparations" in Remington's Pharmaceutical Sciences, pp. 1545-1569, 18th Ed., Mack Printing Company, Easton, Pennsylvania, USA. 1990.
Broadhead, "Chapter 9: Parental Dosage Forms" in Pharmaceutical Preformulation and Formulation: A practical Guide from Candidate Drug Selection to Commercial Dosage Form, pp. 325-347, 2nd Ed., vol. 199, Informa Healthcare, New York, New York, USA . . . 2009.
Butler et al., "Removal of Dissolved Oxygen from Water: A Comparison of Four Common Techniques", Talanta, vol. 41, No. 2, pp. 211-215. 1994.
Connors et al., "Chapter 5: Oxidation" in Chemical Stability of Pharmaceuticals: A Handbook for Pharmacists, pp. 80-98, John Wiley & Sons, New York, USA. 1979.
Cozzi et al., "Synthesis and Characterization of High-Purity N,N-Dimethyltryptamine Hemifumarate for Human Clinical Trials", Drug Test Anal., vol. 12, pp. 1483-1493. 2020.
Human Metabolome Database, Showing Metabocard for Dimethyltryptamine (HMDB0005973), 6 pages, Updated Feb. 26, 2020.
Imitrex Product Insert, Highlights of Prescribing Information, 35 pages, revised Nov. 2015.
Budavari et al. The Merck Index, Print Version, Twelfth Edition: An encyclopedia of chemicals, drugs, and biologicals, 1 page. 1996.
Strassman et al., "Differential Tolerance to Biological and Subjective Effects of Four Closely Spaced Doses of N,N-Dimethyltryptamine in Humans", Biol. Psychiatry, vol. 39, pp. 784-795. 1996.
Timmermann et al., "Neural Correlates of the DMT Experience Assessed with Multivariate EEG", Scientific Reports, Nature Research, vol. 9, 13 pages. 2019.
Uthaug et al., "A Comparison of Reactivation Experiences Following Vaporization and Intramuscular Injection (IM) of Synthetic 5-Methoxy-N,N-Dimethyltryptamine (5-MeO-DMT) in a Naturalistic Setting", Journal of Psychedelic Studies, vol. 4, No. 2, pp. 104-113. 2020.
Waterman et al., "Stabilization of Pharmaceuticals to Oxidative Degradation" Pharmaceutical Development and Technology, vol. 7(1), pp. 1-32. 2002.

* cited by examiner

INJECTABLE AND INHALABLE FORMULATIONS

CROSS REFERENCE TO RELATED APPLICATIONS

This application claims benefit of priority to International Application No. PCT/EP2022/055324 filed Mar. 2, 2022, International Application No. PCT/EP2021/082227 filed Nov. 18, 2021, Taiwan Application No. 110143066 filed Nov. 18, 2021, and United Kingdom Application No. GB 2119021.0 filed Dec. 24, 2021, the entire disclosures of each of which are incorporated by reference herein.

FIELD OF THE INVENTION

The present invention relates to aqueous pharmaceutical formulations, methods for their production, and uses thereof. The aqueous pharmaceutical formulations comprise a salt of an optionally substituted dimethyltryptamine compound and water, with a pH from 5 to 6.5, and a concentration of the optionally substituted dimethyltryptamine compound of about 10 mg/ml or greater as the freebase equivalent. The formulations may have a pH of from about 5 to about 6, or a pH of from 5 to 6. These formulations comprise an effective dose of an optionally substituted dimethyltryptamine compound for use in psychedelic assisted therapy within a volume of 5 ml or less. Such formulations are surprisingly suitable both for intramuscular (IM) injection and nebulised inhalation, being both stable and clinically acceptable, and have potential uses in the treatment of psychiatric or neurological disorders.

BACKGROUND OF THE INVENTION

Classical psychedelics have shown preclinical and clinical promise in treating psychiatric disorders (Carhart-Harris and Goodwin, *Neuropsychopharmacology* 42, 2105-2113 (2017)). In particular, psilocybin has demonstrated significant improvement in a range of depression and anxiety rating scales in randomised double blind studies (Griffiths et al. *Journal of Psychopharmacology*, 30(12), 1181-1197 (2016)).

N,N-dimethyltryptamine (DMT) is also understood to hold therapeutic value as a short-acting psychedelic. A review of research into the biosynthesis and metabolism of DMT in the brain and peripheral tissues, methods and results for DMT detection in body fluids and the brain is provided by S. A. Barker in *Front. Neurosci.*, 12, 536, 1-17 (2018). Barker et al, suggest that 'Further characterization of DMT cellular distribution, receptors and general biochemistry may lead to new targets for more effective pharmaceutical substances and interventions.'

The injection of saline solutions of DMT fumarate salts into human volunteers is described in C. Timmermann et al., *Sci. Rep.*, 9, 16324 (2019). The effect of DMT fumarate on the power spectrum and signal diversity of human brain activity was recorded via multivariate EEG and compared with the results obtained on injection of a placebo (saline solution). It was found that, relative to the results obtained with the placebo, DMT fumarate suppressed alpha power and normalized/increased delta and theta power. Alpha power has been linked with high-level psychological functioning, top-down predictive processing and related feedback connectivity, whilst theta and delta power is classically associated with REM sleep dreaming and related 'visionary' states. It is described that these results relate injection of DMT fumarate to the experience of feeling profoundly immersed in an entirely other world.

Silviera et al (Molecules, 2020, 25, 2072) discuss the stability profile of ayahuasca. Piries et al (Phytochem. Anal. 2009, 20, 149-153) discuss a method for simultaneous determination of the main active constituents found in samples of ayahuasca tea.

According to the Human Metabolome Database (HMDB), N,N-dimethyltryptamine degrades relatively quickly in solution (see specifically http://www.hmdb.ca/metabolites/HMDB0005973). Consequently, there is a need in the art for injectable solutions of DMT that are stable over longer periods of time, and are clinically acceptable, and are formulated in a manner that minimises discomfort and costs associated with administering dimethyltryptamine-based medicines. The present invention addresses this need.

SUMMARY OF THE INVENTION

The present invention relates to aqueous pharmaceutical formulations suitable for both intramuscular injection and nebulised inhalation, comprising about 10 mg/ml or greater (as freebase equivalent) of a salt of an optionally substituted dimethyltryptamine compound, and water, wherein the formulations have pH values of from 5 to 6.5 and typical osmolalities of from about 250 to about 350 mOsm/Kg. The formulations may have a pH of from about 5 to about 6, or a pH of from 5 to 6. These formulations are capable of delivering an effective dose of an optionally substituted dimethyltryptamine compound for use in psychedelic assisted therapy (pharmacological-assisted psychotherapy) within a volume of 5 ml or less, making them particularly suitable for both intramuscular injection and nebulised inhalation. Preferably, the formulations are capable of delivering an effective dose of an optionally substituted dimethyltryptamine compound for use in psychedelic assisted therapy within a volume of 4 ml or less, 3 ml or less, 2.5 ml or less, 2 ml or less, 1 ml or less, or 0.5 ml or less.

The present invention addresses the problem of providing pharmaceutical formulations suitable for intramuscular injection or nebulised inhalation with substantially reduced degradation products compared with known formulations when stored under standard or stressed conditions. This is indicative of improved shelf-life over such known pharmaceutical formulations. Moreover, deuterated optionally substituted dimethyltryptamine compounds, such as deuterated compounds of Formula IA or IB, show significantly improved exposure and Cmax by intramuscular injection, compared with their undeuterated analogues (see FIGS. 1A and 1B). Thus, the present invention provides for the first time an aqueous pharmaceutical formulation with an effective dose (for at least an average weight human) of an optionally substituted dimethyltryptamine compound via intramuscular injection or nebulised inhalation with a volume of 5 ml or less, preferably 4 ml or less, or 3 ml or less, or 2.5 ml or less, or 2 ml or less, or 1 ml or less, or 0.5 ml or less.

Accordingly, viewed from a first aspect, the invention provides a pharmaceutical formulation suitable for both intramuscular injection and nebulised inhalation, comprising a salt of an optionally substituted dimethyltryptamine compound, a base agent, water; and optionally a buffer which is separate to the salt; wherein the formulation has a pH of from about 5 to about 6.5, a concentration of about 10 mg/ml as freebase or greater, and an osmolality of from about 250 to about 350 mOsm/Kg. The formulation may have a pH of from about 5 to about 6, or a pH of from 5 to 6.

In some embodiments of the first aspect of the invention, the formulation comprises from about 10 mg/ml to about 150 mg/ml, from about 10 mg/ml to about 100 mg/ml, from about 10 mg/ml to about 80 mg/ml, from about 15 mg/ml to about 70 mg/ml, from about 15 mg/ml to about 50 mg/ml, or from about 20 mg/ml to about 40 mg/ml (as freebase equivalent) of a salt of an optionally substituted dimethyltryptamine compound. Typically, the formulation comprises about 25 mg/ml (as freebase equivalent) of a salt of an optionally substituted dimethyltryptamine compound.

In preferred embodiments of the first aspect of the present invention, the pharmaceutical formulation comprises an effective dose of an optionally substituted dimethyltryptamine compound for use in psychedelic assisted therapy within a volume of 5 ml or less, preferably within a volume of 4 ml or less, 3 ml or less, 2.5 ml or less, 2 ml or less, 1 ml or less, or 0.5 ml or less.

Viewed from a second aspect, the invention provides a kit suitable for preparing a formulation of the first aspect, said kit comprising a salt of an optionally substituted dimethyltryptamine compound; a base agent, optionally a buffer which is separate to the salt, and optionally a tonicity agent and/or pH adjuster. In preferred embodiments of the second aspect of the present invention, the kit comprises an effective dose of an optionally substituted dimethyltryptamine compound for use in psychedelic assisted therapy within a volume of 5 ml or less, preferably within a volume of 4 ml or less, 3 ml or less, 2.5 ml or less, 2 ml or less, 1 ml or less, or 0.5 ml or less.

Viewed from a third aspect, the invention provides a method of preparing a pharmaceutical formulation of the first aspect, comprising contacting the salt, water, a base agent, optionally a buffer which is separate to the salt, and optionally a tonicity agent and/or pH adjuster. In preferred embodiments of the third aspect of the present invention, the formulation comprises an effective dose of an optionally substituted dimethyltryptamine compound for use in psychedelic assisted therapy within a volume of 5 ml or less, preferably within a volume of 4 ml or less, 3 ml or less, 2.5 ml or less, 2 ml or less, 1 ml or less, or 0.5 ml or less.

In some embodiments, the formulation or kit of the first and second aspect comprises a tonicity agent. In some embodiments, the formulation or kit of the first and second aspect comprises a pH adjuster. In some embodiments, the formulation or kit of the first and second aspect comprises a buffer. In some embodiments, the formulation or kit of the first and second aspect comprises a buffer and a tonicity agent. In some embodiments, the formulation or kit of the first and second aspect comprises a buffer and a pH adjuster. In some embodiments, the formulation or kit of the first and second aspect comprises a buffer, a tonicity agent and a pH adjuster.

Owing to the known instability of the free base of N,N-dimethyltryptamine in solution, solutions comprising optionally substituted dimethyltryptamine compounds are generally prepared immediately before or close to the time of use, i.e. storage of solutions of optionally substituted dimethyltryptamine compounds is avoided. Alternatively, solutions of optionally substituted dimethyltryptamine compounds are frozen. The inventors have found that when a buffer, which is separate to the salt, is used, the resultant formulations are more stable than formulations prepared without a buffer separate to the salt. In addition, when a container adapted to prevent penetration of ultraviolet light is used, the resultant formulations are more stable than those stored in containers that allow for ultraviolet light penetration.

Viewed from a fourth aspect, the invention provides a formulation of the first aspect or kit of the second aspect for use as a medicament or for use in combination with psychotherapy.

Viewed from a fifth aspect, the invention provides a formulation of the first aspect or kit of the second aspect for use in a method of treating a psychiatric or neurological disorder in a patient.

Viewed from a sixth aspect, the invention provides a method of treating a psychiatric or neurological disorder comprising administering to a patient in need thereof a formulation of the first aspect.

Viewed from a seventh aspect, the invention provides a method of treating a psychiatric disorder comprising administering to a patient in need thereof a formulation of the first aspect in combination with psychotherapy.

Viewed from an eighth aspect, the invention provides an aqueous pharmaceutical formulation comprising a salt comprising a Brønsted acid having a pKa at 25° C. of from about 3 to about 5, and a compound of Formula IA

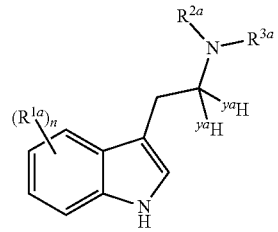

Formula IA wherein:

$R^{1a}$ is independently selected from —$R^{4a}$, —OH, —$OR^{4a}$, —$O(CO)R^{4a}$, monohydrogen phosphate, —F, —Cl, —Br and —I;

n is selected from 0, 1, 2, 3 or 4;

$R^{2a}$ is $C(^{xa}H)_3$;

$R^{3a}$ is $C(^{xa}H)_3$;

each $R^{4a}$ is independently selected from $C_1$-$C_4$alkyl; and each $^{xa}H$ and $^{ya}H$ is independently selected from protium or deuterium;

and water, with a pH from about 5 to about 6.5, and a concentration of the compound of Formula IA of about 10 mg/ml or greater as the freebase equivalent salt. Preferably, the formulation may have a pH of from about 5 to about 6, or a pH of from 5 to 6. In preferred embodiments of the eighth aspect of the present invention, the pharmaceutical formulation comprises an effective dose of a compound of Formula IA for use in psychedelic assisted therapy within a volume of 5 ml or less, preferably within a volume of 4 ml or less, 3 ml or less, 2.5 ml or less, 2 ml or less, 1 ml or less, or 0.5 ml or less.

Viewed from a ninth aspect, the invention provides an aqueous pharmaceutical formulation comprising a salt comprising a Brønsted acid having a pKa at 25° C. of from about 3 to about 5, and a compound of Formula IB Formula IB

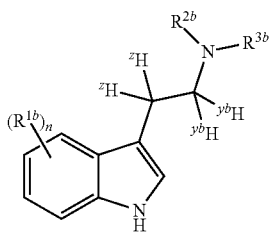

wherein:
R$^{1b}$ is independently selected from —R$^{4b}$, —OH, —OR$^{4b}$, —O(CO)R$^{4b}$, monohydrogen phosphate, —F, —Cl, —Br and —I;
n is selected from 0, 1, 2, 3 or 4;
R$^{2b}$ is C($^{xb}$H)$_3$;
R$^{3b}$ is C($^{xb}$H)$_3$;
each R$^{4b}$ is independently selected from C$_1$-C$_4$alkyl; and
each $^{xb}$H, $^{yb}$H and $^{z}$H is independently selected from protium or deuterium:

and water, with a pH from about 5 to about 6.5, and a concentration of the compound of Formula IB of about 10 mg/ml or greater as the freebase equivalent salt. Preferably, the formulation may have a pH of from about 5 to about 6, or a pH of from 5 to 6. In preferred embodiments of the ninth aspect of the present invention, the pharmaceutical formulation comprises an effective dose of a compound of Formula IB for use in psychedelic assisted therapy within a volume of 5 ml or less, preferably within a volume of 4 ml or less, 3 ml or less, 2.5 ml or less, 2 ml or less, 1 ml or less, or 0.5 ml or less. For the avoidance of doubt, embodiments of the eighth aspect of the invention apply mutatis mutandis to the ninth aspect of the invention.

Viewed from a tenth aspect, the invention provides a lyophilised powder formulation comprising a formulation as defined in the first aspect of the invention which has been lyophilised.

Viewed from an eleventh aspect, the invention provides a method of preparing a lyophilised powder formulation comprising drying the formulation as defined in the first aspect of the invention by lyophilisation.

Viewed from a twelfth aspect, the invention provides a method of preparing an aqueous formulation comprising mixing the lyophilised powder formulation as defined in the tenth aspect or as prepared in the method of the eleventh aspect into water to provide a formulation comprising the salt of an optionally substituted dimethyltryptamine compound, the base agent, water, and optionally the buffer which is separate to the salt to provide a formulation having a pH of from about 5 to about 6.5, a concentration of about 10 mg/ml as freebase or greater, and an osmolality of from about 250 to about 350 mOsm/Kg. Preferably, the formulation may have a pH of from about 5 to about 6, or a pH of from 5 to 6.

For the avoidance of doubt, embodiments of the first aspect of the invention apply mutatis mutandis to the tenth, eleventh and twelfth aspects of the invention.

For the avoidance of doubt, embodiments related to each aspect of the invention apply mutatis mutandis to the other aspects of the invention.

Further aspects and embodiments of the present invention will be evident from the discussion that follows below.

BRIEF DESCRIPTION OF THE FIGURES

FIG. 1: FIG. 1A—Linear plot, FIG. 1B—Semi-log plot. All three drug substances achieve a Cmax greater than 50 ng/ml, indicative of a therapeutically relevant dose. SPL028i and SPL028viii each demonstrate significantly higher plasma levels at 30 mins compared with undeuterated DMT.

FIG. 2A—Linear plot, FIG. 2B—Semi-log plot, SEM error bars.

DETAILED DESCRIPTION OF THE INVENTION

Figure 1A:
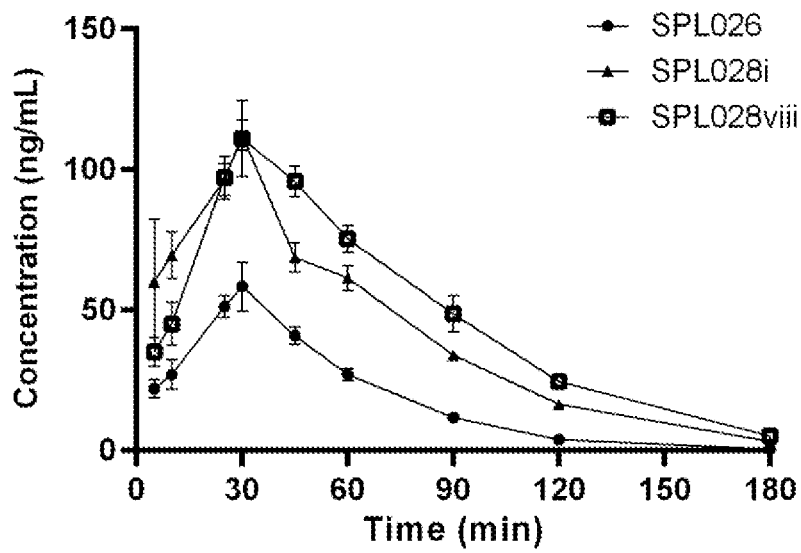
FIG. 1A and FIG. 1B show plots of the mean plasma N,N-Dimethyltryptamine (SPL026), d$_2$-N,N-Dimethyltryptamine (SPL028i) and d$_8$-N,N-Dimethyltryptamine (SPL028viii) concentration over time following 3.5 mg/kg (as fumarate) IM dose; added as a cassette in vivo.

Throughout this specification, one or more aspects of the invention may be combined with one or more features described in the specification to define distinct embodiments of the invention.

Unless otherwise mentioned, measurements are carried out at room temperature and pressure, i.e. 20° C. (293.15 K, 68° F.) and 1 atm (14.696 psi, 101.325 kPa), respectively. Unless otherwise stated, ambient conditions refer to room temperature and pressure.

In the discussion that follows, reference is made to a number of terms, which are to be understood to have the meanings provided below, unless a context expressly indicates to the contrary. The nomenclature used herein for the psychedelic agents for use in the formulations of the invention is as commonly used in the field. The compounds described herein, may also be referred to by nomenclature in accordance with the rules of the International Union of Pure and Applied Chemistry (IUPAC) for chemical compounds, specifically the 'IUPAC Compendium of Chemical Terminology (Gold Book)' (see A. D. Jenkins et al., Pure & Appl. Chem., 1996, 68, 2287-2311). For the avoidance of doubt, if a rule of the IUPAC organisation is contrary to a definition provided herein, the definition herein is to prevail.

References herein to a singular of a noun encompass the plural of the noun, and vice-versa, unless the context implies otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. The term 'comprising' includes within its ambit the term 'consisting' or 'consisting essentially of'.

The term 'consisting' or variants thereof is to be understood to imply the inclusion of a stated element, integer or step, or group of elements, integers or steps, and the exclusion of any other element, integer or step or group of elements, integers or steps.

The term 'consisting essentially of' or variants thereof is to be understood to imply the inclusion of a stated element, integer or step, or group of elements, integers or steps, and that further components may be present, but only those not materially affecting the essential characteristics of the formulation, composition, or compound.

The term 'about' as used herein, when qualifying a number or value, is used to refer to values that lie within ±5% of the value specified. For example, if an osmolality range is specified to be about 250 to about 350 mOsm/Kg, values of 238 to 367 are included; of a pH range is specified to be about 5 to about 6, values of 4.75 to 6.3 are included. For the avoidance of doubt, where a number or value is specified herein in the absence of the term 'about', the number or value should be understood according to standard numeric rounding conventions according to the number of decimal places. For example, a whole number, such as 6, is understood to encompass values ≥5.5 and <6.5. Likewise, a number specified to one decimal place, such as 5.3, is understood to encompass values ≥5.25 and <5.35.

The term 'aqueous' as used herein refers to a formulation that comprises water and may also comprise additional solvents.

The formulations of the invention are useful in therapy and may be administered to a patient in need thereof. As used herein, the term 'patient' preferably refers to a mammal. Typically, the mammal is a human, but may also refer to a domestic mammal. The term does not encompass laboratory mammals.

As used herein, the term 'effective does' refers to a dose which, on average, elicits a clinical response, i.e. an improvement in symptoms.

As used herein, the term 'in combination with psychotherapy' refers to the treatment of a psychiatric disorder by psychological means, which are enhanced by administration of a formulation of the invention. The terms 'psychedelic assisted therapy' and 'pharmacological assisted therapy' are used herein to refer to treatment in combination with psychotherapy.

The term 'treatment' defines the therapeutic treatment of a patient, in order to reduce or halt the rate of progression of a disorder, or to ameliorate or cure the disorder. Prophylaxis of a disorder as a result of treatment is also included. References to prophylaxis are intended herein not to require complete prevention of a disorder: its development may instead be hindered through treatment in accordance with the invention. Typically, treatment is not prophylactic, and the formulation is administered to a patient having a diagnosed or suspected disorder.

As is understood in the art, psychiatric or neurological disorders are disorders which may be associated with one or more cognitive impairment. As used herein, the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom.

Diagnostic criteria for psychiatric or neurological disorders referred to herein are provided in the Diagnostic and Statistical Manual of Mental Disorders, Fifth Edition, (DSM-5).

As used herein the term 'psychedelic assisted therapy', is defined as any psychological therapeutic practice that is provided alongside a psychedelic therapeutic formulation, including for example any formulation defined by the present invention.

As used herein the term 'obsessive-compulsive disorder' (OCD) is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically, OCD manifests as one or more obsessions, which drive adoption of a compulsion. For example, an obsession with germs may drive a compulsion to clean or an obsession with food may drive a compulsion to overeat, eat too little or throw up after eating (i.e. an obsession with food may manifest itself as an eating disorder). A compulsion can either be overt and observable by others, such as checking that a door is locked, or a covert mental act that cannot be observed, such as repeating a certain phrase in one's mind.

As used herein, the term 'eating disorder' is defined by severe and persistent disturbance in eating behaviours and associated distressing thoughts and emotions. The term 'eating disorder' includes anorexia nervosa and bulimia nervosa, binge eating disorder, avoidant restrictive food intake disorder, other specified feeding and eating disorder, pica and rumination disorder.

Eating disorders often co-occur with anxiety disorders and obsessive compulsive disorder. Neziroglu and Sandler differentiate between OCD and an eating disorder: 'Whereas patients with eating disorders are primarily driven by concerns of physical appearance, and consequently alter their eating patterns in order to lose weight accordingly. OCD patients may be restricting their eating for reasons very different than body image concerns' (https://iocdf.orq/expert-opinions/expert-opinion-eatinq-disorders-and-ocd/).

The invention provides a formulation or kit according to the first and second aspect of the invention for use in a method of treating an eating disorder. The term 'eating disorder' includes anorexia nervosa, bulimia and binge eating disorder (BED). The symptoms of anorexia nervosa include eating too little and/or exercising too much in order to keep weight as low as possible. The symptoms of bulimia include eating a lot of food in a very short amount of time (i.e. binging) and then being deliberately sick, using laxatives, eating too little and/or exercising too much to prevent weight gain. The symptoms of BED include regularly eating large portions of food until uncomfortably full, and consequently feeling upset or guilty.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:
  depressed mood, such as feeling sad, empty or tearful (in children and teens, depressed mood can appear as constant irritability);
  significantly reduced interest or feeling no pleasure in all or most activities;
  significant weight loss when not dieting, weight gain, or decrease or increase in appetite (in children, failure to gain weight as expected);
  insomnia or increased desire to sleep;
  either restlessness or slowed behaviour that can be observed by others;
  fatigue or loss of energy;
  feelings of worthlessness, or excessive or inappropriate guilt;
  trouble making decisions, or trouble thinking or concentrating;
  recurrent thoughts of death or suicide, or a suicide attempt.

At least one of the symptoms must be either a depressed mood or a loss of interest or pleasure.

Persistent depressive disorder, also known as dysthymia, is defined as a patient exhibiting the following two features:
A. has depressed mood for most the time almost every day for at least two years. Children and adolescents may have irritable mood, and the time frame is at least one year.
B. While depressed, a person experiences at least two of the following symptoms:
Either overeating or lack of appetite.
Sleeping too much or having difficulty sleeping.
Fatigue, lack of energy.
Poor self-esteem.
Difficulty with concentration or decision-making.

As used herein the term 'treatment resistant major depressive disorder' describes MDD that fails to achieve an adequate response to an adequate treatment with standard of care therapy.

As used herein, 'bipolar disorder', also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely 'up,' elated, and energised behaviour (known as manic episodes, and defined further below) to very sad, 'down,' or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein, the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein, the term 'post-partum depression' (PPD, also known as postnatal depression) is a form of depression experienced by either parent of a newborn baby. Symptoms typically develop within 4 weeks of delivery of the baby and often include extreme sadness, fatigue, anxiety, loss of interest or pleasure in hobbies and activities, irritability, and changes in sleeping or eating patterns.

As used herein, the term 'substance abuse' means a patterned use of a drug in which the user consumes the substance in amounts or with methods that are harmful to themselves or others.

As used herein, the term 'gambling disorder' means persistent and recurrent problematic gambling behaviour leading to clinically significant impairment or distress. The disorder has similarities with substance abuse.

As used herein, the term 'an avolition disorder' refers to a disorder that includes as a symptom the decrease in motivation to initiate and perform self-directed purposeful activities.

The invention provides an aqueous pharmaceutical formulation suitable for either intramuscular injection and/or nebulised inhalation, comprising a salt of an optionally substituted dimethyltryptamine compound; a base agent; water; and optionally a buffer which is separate to the salt; wherein the formulation has a pH of from about 5 to about 6.5, and an osmolality of from about 250 to about 350 mOsm/Kg. The formulation may have a pH of from about 5 to about 6, or a pH of from 5 to 6.

In preferred embodiments of the invention, the pharmaceutical formulation comprises an effective dose of an optionally substituted dimethyltryptamine compound for use in psychedelic assisted therapy within a volume of 5 ml or less, preferably within a volume of 4 ml or less, 3 ml or less, 2.5 ml or less, 2 ml or less, 1 ml or less, or 0.5 ml or less.

The inventors have found that the formulation is surprisingly more stable than formulations prepared at higher pH (specifically those prepared at a pH matching human blood serum, i.e. at a pH of about 7.4). The greater stability of the formulation of the invention relative to the isotonic formulation is discussed in more detail in the Examples section.

Osmolality is formally defined as the quotient of the negative natural logarithm of the rational activity of water and the molar mass of water, as represented by formula:

$$\text{osmolality} = \frac{-\ln a_w}{18.015}; a_w = \frac{p}{p^*}$$

where p is the partial vapour pressure of water in the solution and p* is the partial vapour pressure of pure water. In simpler terms, osmolality is the number of osmotically active particles (the number of solute particles) in 1 kg of a solution. Thus, osmolality is a function only of the number of particles, and is not related to particle molecular weight, size, shape, or charge (see D. K. Faria et al., M. E. Mendes and N. M. Sumita, *J. Bras. Patol. Med. Lab.,* 53, 1, 38-45 (2017) for a review of the measurement of serum osmolality). For example, one mole of a nondissociating substance (e.g. DMT as a free base) dissolved in 1 kg of water has an osmolality of 1 Osm/kg (1000 mOsm/kg), whilst one mole of a substance that dissociates into two separate species in solution (e.g. DMT fumarate) dissolved in 1 kg of water has an osmolality of 2 Osm/kg (2000 mOsm/kg).

Where a first solution is defined herein to be isotonic with a second solution, the solutions have the same osmolality. For example, where a formulation is defined to be isotonic with human blood serum, the formulation has the same osmolality as human blood serum. Human blood serum typically has an osmolality of about 275 to about 300 mOsm/Kg (L. Hooper et al., *BMJ Open,* 2015; 5(10): e008846).

The formulation of the invention is suitable for nebulised inhalation. Typically, the particles present in the formulation for nebulised inhalation have a mass mean aerodynamic diameter (MMAD) of from about 0.1 to about 10 μm, preferably from about 0.3 to about 8 μm, preferably from about 0.3 to about 7 μm, more preferably from about 0.5 to about 5 μm or from about 3 to about 7 μm. The MMAD will be selected according to the type of nebuliser, such as a jet nebuliser, mesh nebuliser or an ultrasonic nebuliser. Suitably, a multistage cascade impactor (CI) apparatus may be used to size fractionate aerosols in terms of their aerodynamic particle size distributions (APSDs). The MMAD is calculated from the APSD and is defined as the diameter at which 50% of the particles of an aerosol by mass are larger and 50% are smaller.

The formulation (i.e. of the invention) is suitable for intramuscular injection, by which is meant that it is in accordance with Pharmacopeial requirements of sterility, contaminants, and pyrogens (see for example The United States Pharmacopeial Convention, General Requirements/ <1> Injections, page 33). Sometimes, the formulation contains inhibitors of the growth of microorganisms (e.g. antimicrobial preservatives) and/or anti-oxidants.

Formulations suitable for parenteral administration generally have a pH of about 3 to 9 and an osmolality of about 250 to about 600 mOsm/Kg. pH values above 9 are reported by I. Usach et al. in *Adv. Ther.,* 36, 2986-2996 (2019) to relate to tissue necrosis (death of cells within the tissue), whereas values lower than 3 are reported to cause pain and phlebitis (inflammation of veins). However, Usach et al report 'a pH close to the physiological one is recommended to minimize pain, irritation, and tissue damage' (emphasis added). Osmolality values greater than 600 mOsm/Kg are also reported to cause pain. Usach et al also recommend that parenteral formulations should be formulated as isotonic solutions (osmolality of about 300 mOsm/Kg), proposing an upper limit of 600 mOsm/Kg to minimise pain.

The formulation (i.e. of the invention) is also suitable for inhalation, particularly for nebulised inhalation.

The formulation comprises a salt of an optionally substituted dimethyltryptamine compound. Formulations in accordance with this invention may comprise one or more than one salt of an optionally substituted dimethyltryptamine compound. For the avoidance of doubt, formulations comprise an optionally substituted dimethyltryptamine salt when they comprise ions of an optionally substituted dimethyltryptamine compound and ions that counter the charge of the optionally substituted dimethyltryptamine ions (counterions). Accordingly, the optionally substituted dimethyltryptamine salt within the formulation may be formed, for example, by contacting optionally substituted dimethyltryptamine as a free base with an aqueous solution comprising an excess of buffer relative to the molar quantity of optionally substituted dimethyltryptamine.

The dimethyltryptamine compound is optionally substituted with deuterium, wherein a deuterium atom is a hydrogen atom with an additional neutron.

In some embodiments, the dimethyltryptamine compound is substituted at position 4 or 5 with acetoxy or methoxy or at position 4 with monohydrogen phosphate. The term 'acetoxy' (often abbreviated to OAc) defines a univalent group derived from acetic acid by removal of a hydrogen atom from the OH moiety. The term 'methoxy' (often abbreviated to OMe) defines a univalent group derived from methanol by removal of a hydrogen atom from the OH moiety. The term monohydrogen phosphate defines a divalent group of formula $HPO_4$, derived from phosphoric acid by removal of a proton from two of the three OH moieties, and thus denotes a substituent of formula —OP(O)(OH)$O^-$.

Where the dimethyltryptamine compound is substituted at position 4 with monohydrogen phosphate, this is to reflect that psilocybin (also known as [3-(2-Dimethylaminoethyl)-1H-indol-4-yl] dihydrogen phosphate) in water generally has monohydrogen phosphate at the 4-position, this generally being understood to be the predominant form owing to the pKa values of the two terminal phosphate oxygen atoms being estimated as 1.3 and 6.5. It is further understood that the monohydrogen phosphate-containing form of psilocybin exists as a zwitterion (i.e. an internal salt) in which the nitrogen atom of the dimethylamino moiety is protonated. This form is thus, and psilocybin is to be regarded as, a salt of a dimethyltryptamine compound substituted at position 4 with monohydrogen phosphate.

For the avoidance of doubt, positions 4 and 5 of the optionally substituted dimethyltryptamine salt refer to the positions labelled in the structure below (substitution not shown).

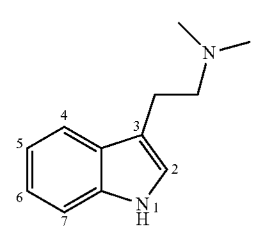

The formulation optionally comprises a buffer, which is separate to the salt, i.e. the buffer is not merely a counterion to the optionally substituted dimethyltryptamine. For example, where the salt is N,N-dimethyltryptamine fumarate (i.e. the fumaric acid salt of N,N-dimethyltryptamine), an amount of buffer may be required over and above the buffer effect provided by the fumarate salt. The term 'buffer' is well known in the art and refers to a chemical which, on inclusion within a formulation, resists a change in pH on addition of acid or base to the formulation. As used herein, the term 'buffer' refers to the buffer system or the buffer agent. Suitable buffer systems for use in the formulations of the invention comprise a weak acid and its conjugate base. A suitable buffer system comprises an acid with a pKa value that lies within ±1 of the desired pH of the formulation. For example, if the desired pH of the formulation is about 5.0, a suitable buffer system comprises a weak acid with a pKa value of from about 4.0 to about 6.0. If the acid of a buffer system has more than one pKa value (i.e. each molecule of the acid is able to donate more than one proton), in order for the buffer to be suitable, at least one of the pKa values lies within the desired pH range.

The weak acid and conjugate base of the buffer system are in equilibrium with one another. In accordance with Le Chatelier's principle (if a constraint (such as a change in concentration of a reactant) is applied to a system in equilibrium, the equilibrium will shift so as to counteract the effect of the constraint), addition of acid or base to the formulation shifts the position of equilibrium in favour of the conjugate base or weak acid, respectively. Consequently, the concentration of free protons in the formulation (and thus the pH) is relatively unchanged.

As described above, the formulation of the invention has a pH of from about 5 to about 6.5, preferably from about 5 to about 6, preferably from about 5.0 to about 6.0. Preferably, the pH is from 5 to 6, preferably from 5.0 to 6.0. Preferably, the pH is from about 5.2 to about 5.8, or about 5.5 to 6.0. Preferably the pH is from about 5.7 to about 6.5, or about 5.7 to about 6. More preferably, the pH is about 5.5 or about 6.

In some embodiments, the formulation comprises a buffer. In some embodiments, the buffer is separate to the salt.

Suitable buffer systems comprise an acetate salt and acetic acid (pKa=4.75); a citrate salt and citric acid (pKa=3.13, 4.76 and 6.40); and phosphoric acid (pKa=2.14, 7.20 and 12.37); or mixtures thereof. The pKa values cited herein are those reported at 25° C. in water. Typically, the buffer system comprises only one of the pairs listed above, i.e. one acid and its conjugate base.

In some embodiments, the buffer system comprises an acetate salt and acetic acid; a citrate salt and citric acid; or a phosphate salt and phosphoric acid.

Sometimes, the buffer system comprises an acetate salt and acetic acid; or a citrate salt and citric acid.

In some embodiments, the buffer system comprises an acetate salt and acetic acid, often sodium acetate and acetic acid, or potassium acetate and acetic acid.

As used herein, the term 'buffer agent' refers to the weak acid or weak base. Any pharmaceutically acceptable buffer agent may be used in the formulations of the invention, including phosphoric acid, citric acid, acetic acid, phosphate salt, citrate salt, and acetate salt. In some embodiments, the buffer comprises sodium phosphate, sodium citrate, or sodium acetate.

Preferably, the pharmaceutical formulation comprises an effective dose of an optionally substituted dimethyltryptamine compound for use as a medicament or for use in psychedelic assisted therapy, meaning that the formulation comprises the salt of the dimethyltryptamine compound in a dose range which elicits a psychedelic experience in an average weight human patient. Typically, the dose range is from about 5 to about 250 mg, or about 10 to about 150 mg, suitably from about 10 to about 100 mg, suitably from about 20 to about 100 mg (as free base equivalent). In some embodiments, the dose range is from about 20 to about 70 mg, or from about 20 to about 50 mg. For example, the suitable dose is about 9 mg, or about 12 mg, or about 17 mg, or about 21.5 mg, or about 24 mg, or about 30.5 mg, or about 34 mg, or about 33 mg, or about 36 mg, or about 38.5 mg, or about 43 mg, or about 51 mg, or about 52 mg, or about 55 mg, or about 60 mg, or about 64.5 mg. The dose ranges and suitable doses provided in this paragraph refer to the free base equivalent dose.

The concentration of buffer within the formulation is typically sufficient to resist significant pH change of the formulation on storage of the formulation for two weeks (i.e. the pH typically fluctuates less than about 0.1 pH unit), while also ensuring that the osmolality of the formulation lies within the desired range of from about 250 to about 350 mOsm/Kg. The skilled person is able to assess suitable buffer concentrations and to achieve this. Often, the concentration of buffer is from about 15 mM to about 75 mM, such as about 20 mM to about 30 mM. In some embodiments, the concentration of the buffer is about 25 mM.

As described above, the formulation comprises a salt of an optionally substituted dimethyltryptamine compound at a concentration of about 10 mg/ml or greater as the freebase equivalent.

The salt comprises an acid and the optionally substituted dimethyltryptamine compound, or the salt comprises a dimethyltryptamine compound substituted with monohydrogen phosphate, preferably at position 4 of the indole ring system. An example of a salt comprising an acid and dimethyltryptamine compound is N,N-dimethyltryptamine fumarate, which is the fumaric acid salt of N,N-dimethyltryptamine. P. H. Stahl and C. G. Wermuth provide an overview of pharmaceutical salts and the acids comprised therein in *Handbook of Pharmaceutical Salts: Properties, Selection and Use*, Weinheim/Zürich:Wiley-VCH/VHCA, 2002. The acids described in this review are suitable acids for inclusion within the salt of the formulation.

The salt may comprise an acid selected from the group consisting of fumaric acid, tartaric acid, citric acid, acetic acid, lactic acid, gluconic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid, aspartic acid, benzenesulfonic acid, benzoic acid, camphoric acid, camphor-10-sulfonic acid, decanoic acid, hexanoic acid, octanoic acid, carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, glucuronic acid, glutamic acid, glutaric acid, glycerophosphoric acid, glycolic acid, hippuric acid, hydrobromic acid, hydrochloric acid, isobutyric acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (–L), salicylic acid, sebacic acid, stearic acid, succinic acid, sulfuric acid, thiocyanic acid, toluenesulfonic acid and undecylenic acid.

In some embodiments, where the salt comprises an acid and the dimethyltryptamine compound, the acid is a Brønsted acid having a pKa at 25° C. in water of from about 3 to about 5. In these embodiments, the Brønsted acid may act both as a counterion to the dimethyltryptamine compound and as a buffer. Thus, the formulation may be stabilised to a greater extent, i.e. degradation of the dimethyltryptamine compound may be further ameliorated, when the salt comprises such an acid.

In some embodiments, the salt comprises a Brønsted acid having a pKa at 25° C. of from about 3 to about 5, and a compound of Formula IA

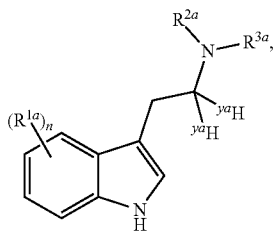

Formula IA wherein:
$R^{1a}$ is independently selected from —$R^{4a}$, —OH, —$OR^{4a}$, —$O(CO)R^{4a}$, monohydrogen phosphate, —F, —Cl, —Br and —I;
n is selected from 0, 1, 2, 3 or 4;
$R^{2a}$ is $C(^{xa}H)_3$;
$R^{3a}$ is $C(^{xa}H)_3$;
each $R^{4a}$ is independently selected from $C_1$-$C_4$alkyl; and
each $^{xa}H$ and $^{ya}H$ is independently selected from protium or deuterium.

In some embodiments, the salt comprises a Brønsted acid having a pKa at 25° C. of from about 3 to about 5, and a compound of Formula IB

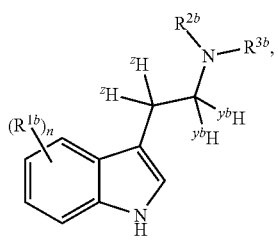

Formula IB wherein:
$R^{1b}$ is independently selected from —$R^{4b}$, —OH, —$OR^{4b}$, —$O(CO)R^{4b}$, monohydrogen phosphate, —F, —Cl, —Br and —I;
n is selected from 0, 1, 2, 3 or 4;
$R^{2b}$ is $C(^{xb}H)_3$;
$R^{3b}$ is $C(^{xb}H)_3$;
each $R^{4b}$ is independently selected from $C_1$-$C_4$alkyl; and
each $^{xb}H$, $^{yb}H$ and $^{z}H$ is independently selected from protium or deuterium.

In some embodiments, the compound is of (i) Formula IA, wherein each $R^{1a}$ is independently selected from —$OR^{4a}$, —$O(CO)R^{4a}$, monohydrogen phosphate and —OH, or (ii) Formula IB, wherein each $R^{1b}$ is independently selected from —$OR^{4b}$, —$O(CO)R^{4b}$, monohydrogen phosphate and —OH.

It will be recognised that Formula IA is a sub-formula of IB, wherein each $^{z}H$ is hydrogen.

In some embodiments, the compound is of (i) Formula IA, wherein $R^{4a}$ is methyl, or (ii) Formula IB, wherein $R^{4b}$ is methyl.

In some embodiments, the compound is of Formula IA or Formula IB according to any preceding embodiment, wherein n is 1, 2, 3, or 4.

In some embodiments, the compound is of Formula IA or Formula IB according to any preceding embodiment, wherein n is 1.

In some embodiments, the compound is of (i) Formula IA according to any preceding embodiment, wherein n is 0; or n is 1, and $R^{1a}$ is at the 4- or 5-position; or (ii) Formula IB according to any preceding embodiment, wherein n is 0; or n is 1, and $R^{1b}$ is at the 4- or 5-position.

In some embodiments, the compound is of (i) Formula IA according to any preceding embodiment, wherein each $R^{1a}$ is independently selected from —OH, —OMe, —$OCD_3$, —OAc, —O(CO)Me, and monohydrogen phosphate; or (ii) Formula IB, wherein each $R^{1b}$ is independently selected from —OH, —OMe, —$OCD_3$, —OAc, —O(CO)Me, and monohydrogen phosphate.

In some embodiments, the compound is of (i) Formula IA according to any preceding embodiment, wherein n is 0; or n is 1 and $R^{1a}$ is selected from 5-methoxy, 5-bromo, 4-acetoxy, 4-monohydrogen phosphate, 4-hydroxy and 5-hydroxy; or (ii) Formula IB according to any preceding embodiment, wherein n is 0; or n is 1 and $R^{1b}$ is selected from 5-methoxy, 5-bromo, 4-acetoxy, 4-monohydrogen phosphate, 4-hydroxy and 5-hydroxy.

In some embodiments, the compound is of Formula IA or IB, wherein n is 0.

In some embodiments, the compound is of (i) Formula IA according to any preceding embodiment, wherein both $^{ya}H$ are deuterium, or (ii) Formula IB according to any preceding embodiment, wherein both $^{yb}H$ are deuterium.

In some embodiments, the compound is of (i) Formula IA according to any preceding embodiment, wherein both $^{ya}H$ are protium, or (ii) Formula IB according to any preceding embodiment, wherein both $^{yb}H$ are protium.

In some embodiments, the compound is of (i) Formula IA according to any preceding embodiment, wherein one $^{ya}H$ is protium and one $^{ya}H$ is deuterium, or (ii) Formula IB according to any preceding embodiment, wherein one $^{yb}H$ is protium and one $^{yb}H$ is deuterium.

In some embodiments, the compound is of Formula IB, wherein both $^{z}H$ are deuterium. In some embodiments, the compound is of Formula IB, wherein both $^{z}H$ are protium. In some embodiments, the compound is of Formula IB, wherein one $^{z}H$ is protium and one $^{z}H$ is deuterium.

In some embodiments, the compound is of (i) Formula IA according to any preceding embodiment, wherein each $^{xa}H$ is D, or (ii) Formula IB according to any preceding embodiment, wherein each $^{xb}H$ is D. In some embodiments, the compound is of (i) Formula IA according to any preceding embodiment, wherein $R^{2a}$ and $R^{3a}$ are both $C(^{xa}H)_3$, or (ii) Formula IB according to any preceding embodiment, wherein $R^{2b}$ and $R^{3b}$ are both $C(^{xb}H)_3$.

In some embodiments, the compound is of (i) Formula IA according to any preceding embodiment, wherein both $C(^{xa}H)_3$ are the same, or (ii) Formula IB according to any preceding embodiment, wherein both $C(^{xb}H)_3$ are the same.

In some embodiments, the compound is of (i) Formula IA according to any preceding embodiment, wherein both $R^{2a}$ and $R^{3a}$ are $CD_3$, or (ii) Formula IB according to any preceding embodiment, wherein both $R^{2b}$ and $R^{3b}$ are $CD_3$.

In some embodiments, the compound is of (i) Formula IA according to any preceding embodiment, wherein both $R^{2a}$ and $R^{3a}$ are $CH_3$, or (ii) Formula IB according to any preceding embodiment, wherein both $R^{2b}$ and $R^{3b}$ are $CH_3$.

In some embodiments, the compound is of (i) Formula IA according to any preceding embodiment, wherein $R^{2a}$ is $CD_3$ and $R^{3a}$ is $CH_3$, or (ii) Formula IB according to any preceding embodiment, wherein $R^{2b}$ is $CD_3$ and $R^{3b}$ is $CH_3$.

In some embodiments, $C_1$-$C_4$alkyl may be a deuterated $C_1$-$C_4$alkyl, for example $CD_3$.

For the avoidance of doubt, certain optionally substituted dimethyltryptamine compounds comprised in the present invention include compounds which are known by two or more names in the art, including:

The compound N,N-dimethyltryptamine (DMT) may also be known as N,N-dimethyl-1H-indole-3-ethanamine (CAS number 61-50-7).

The compound 5-methoxy-N,N-dimethyltryptamine (5-MeO-DMT) may also be known as 5-methoxy-N,N-dimethyl-1H-indole-3-ethanamine (CAS number 1019-45-0).

The compound 4-acetoxy-N,N-dimethyltryptamine (4-AcO-DMT) may also be known as 4-acetoxy-N,N-dimethyltryptamine, O-acetylpsilocin, psilacetin, or [3-[2-(dimethylamino)ethyl]-1H-indol-4-yl] acetate (CAS number 92292-84-7).

The compound 4-hydroxy-N,N-dimethyltryptamine-$d_6$ may also be known as psilocin-$d_6$ or 3-(2-(bis(methyl-$d_3$)amino)ethyl)-1H-indol-4-ol.

The compound N,N-di(trideuteromethyl)tryptamine may also be known as N,N-hexadeuterio-dimethyltryptamine or $D_6$-DMT.

The compound 5-hydroxy-N-mono(trideuteromethyl)tryptamine may also be known as N-methyl-serotonin-$D_3$ (CAS No. 1794811-18-9).

The compound N-mono(trideuteromethyl)tryptamine may also be known as N-methyl-tryptamine-$D_3$ (CAS No. 1794745-39-0).

The compound α,α-dideutero-N,N-dimethyltryptamine may also be known as $D_2$-DMT, or 2-(1H-indol-3-yl)-N,N-dimethylethan-1-amine-1,1-$d_2$.

The compound α,α,β,β-tetradeutero-N,N-dimethyltryptamine may also be known as $D_4$-DMT, or 2-(1H-indol-3-yl)-N,N-dimethylethan-1-amine-1,1,2,2-$d_4$.

The compound α,α,β,β-tetradeutero-N,N-di(trideuteromethyl)tryptamine may also be known as $D_{10}$-DMT, or 2-(1H-indol-3-yl)-N,N-bis(methyl-$d_3$)ethan-1-amine-1,1,2,2-$d_4$.

In some embodiments, the optionally substituted dimethyltryptamine compound is N,N-dimethyltryptamine. In some embodiments, the optionally substituted dimethyltryptamine compound is a deuterated dimethyltryptamine compound, including α,α-dideutero-N,N-dimethyltryptamine, N,N-di(trideuteromethyl)tryptamine, α,α-dideutero-N,N-di(trideuteromethyl)tryptamine, α,α,β,β-tetradeutero-N,N-dimethyltryptamine, and α,α,β,β-tetradeutero-N,N-di(trideuteromethyl)tryptamine.

Salts of deuterated N,N-dimethyltryptamine compounds, which as defined above can be synthesised following the synthetic schemes disclosed in WO 2020/245133 A1, WO 2021/116503 and WO 2021/089873 A1 (all Small Pharma Ltd), have been found to be particularly advantageous drug substances for formulations of the present invention. Deuterated N,N-dimethyltryptamine compounds as described hereinabove have been found to exhibit a kinetic isotope effect which can be used to extend their half-life in biological systems. The inventors have now found in vivo that formulations of the present invention comprising deuterated N,N-dimethyltryptamine compounds and deuterated substituted N,N-dimethyltryptamine compounds have significantly higher Cmax and exposure relative to their undeuterated analogue (see FIGS. 1A and 1B).

If desired, compositions may be prepared for use in the formulations of the invention comprising amounts of N,N-dimethyltryptamine and deuterated N,N-dimethyltryptamine compounds, wherein the relative proportions of N,N-dimethyltryptamine against deuterated N,N-dimethyltryptamine compounds (as defined above) may be controlled by varying the ratio of lithium aluminium hydride and lithium aluminium deuteride in the reducing agent, as described in WO 2021/116503 (Small Pharma Ltd), for example.

The composition comprising amounts of N,N-dimethyltryptamine and/or deuterated N,N-dimethyltryptamine compounds may be used to provide the salt of an optionally substituted dimethyltryptamine compound, such that the formulation comprises one or more optionally substituted dimethyltryptamine compounds each in the form of a salt as described herein.

The compositions comprised in the formulation may comprise an amount of 90% or greater, 95% or greater, preferably 97% or greater, more preferably 98% or greater, most preferably 99% or greater, α,α-dideutero-N,N-dimethyltryptamine by weight of the composition.

The compositions comprised in the formulation may comprise an amount of 5% or less, preferably 2% or less, more preferably 1% or less, most preferably 0.5% or less, N,N-dimethyltryptamine by weight of the composition.

The compositions comprised in the formulation may comprise an amount of 5% or less, preferably 2% or less, more preferably 1% or less, most preferably 0.5% or less, α-protio-α-deutero-N,N-dimethyltryptamine by weight of the composition.

In some embodiments, the compositions comprised in the formulation may comprise a) 90% or greater of an α,α-dideutero-N,N-dimethyltryptamine compound, b) 10% or less of an α-protio-α-deutero-N,N-dimethyltryptamine compound, and c) 2% or less of N,N-dimethyltryptamine by weight of the composition, wherein the weight of the α,α-dideutero-N,N-dimethyltryptamine compound, the α-protio-α-deutero-N,N-dimethyltryptamine compound, and N,N-dimethyltryptamine total 100%.

In some embodiments, the compositions comprised in the formulation may comprise a) 95% or greater of an α,α-dideutero-N,N-dimethyltryptamine compound, b) 5% or less of an α-protio-α-deutero-N,N-dimethyltryptamine compound, and c) 1% or less of N,N-dimethyltryptamine by weight of the composition, wherein the weight of the α,α-dideutero-N,N-dimethyltryptamine compound, the α-protio-α-deutero-N,N-dimethyltryptamine compound, and N,N-dimethyltryptamine total 100%.

For the avoidance of doubt, N,N-dimethyltryptamine may be absent, or may be present in the composition in trace amounts, or may be present in the composition in an amount 2% or less by weight of the composition, or in an amount 1% or less by weight of the composition. In the case of 4, 5, 6, or 7-substituted dimethyltryptamine compounds, the 2% or less, or 1% or less N,N-dimethyltryptamine referred to above should be understood to encompass, for example undeuterated 4, 5, 6 or 7-substituted N,N-dimethyltryptamines such as 5-methoxy-N,N-dimethyltryptamine. By way of illustration, in compositions comprising 5-methoxy-α,α-dideutero-N,N-dimethyltryptamine, 5-methoxy-N,N-dimethyltryptamine may be absent, or may be present in the composition in trace amounts, or may be present in the composition in an amount 2% or less, or 1% or less, by weight of the composition.

The term 'an α,α-dideutero-N,N-dimethyltryptamine compound' as used herein, comprises the compound α,α-dideutero-N,N-dimethyltryptamine ($d_2$-DMT) as well as α,α-dideutero-N,N-dimethyltryptamine compounds comprising deuteration at other positions, such as α,α,β,β-tetradeutero-N,N-dimethyltryptamine ($d_4$-DMT), α,α-dideutero-N,N-di(trideuteromethyl)tryptamine ($d_8$-DMT), α,α,β,β-tetradeutero-N,N-di(trideuteromethyl)tryptamine ($d_{10}$-DMT), and substituted α,α-dideutero-N,N-dimethyltryptamine compounds such as 5-methoxy-α,α-dideutero-N,N-di(trideuteromethyl)tryptamine.

The term 'an α-protio-α-deutero-N,N-dimethyltryptamine compound' as used herein, comprises the compound α-protio-α-deutero-N,N-dimethyltryptamine ($d_1$-DMT) as well as α-protio-α-deutero-N,N-dimethyltryptamine compounds comprising deuteration at other positions, such as α-protio-α,β,β-trideutero-N,N-dimethyltryptamine ($d_3$-DMT), α-protio-α-deutero-N,N-di(trideuteromethyl)tryptamine ($d_7$-DMT), α-protio-α,β,β-trideutero-N,N-di(trideuteromethyl)tryptamine ($d_9$-DMT), and substituted α-protio-α-deutero-N,N-dimethyltryptamine compounds such as 5-methoxy-α-protio-α-deutero-N,N-di(trideuteromethyl)tryptamine. In some embodiments, the compositions comprised in the formulation may comprise a) 90% or greater of an optionally substituted N,N-di(trideuteromethyl)tryptamine compound, preferably 95% or greater. The optionally substituted N,N-di(trideuteromethyl)tryptamine compound may be N,N-di(trideuteromethyl)tryptamine ($d_6$-DMT), α,α-dideutero-N,N-di(trideuteromethyl)tryptamine ($d_8$-DMT), α,α,β,β-tetradeutero-N,N-di(trideuteromethyl)tryptamine ($d_{10}$-DMT), 5-methoxy-N,N-di(trideuteromethyl)tryptamine, 5-methoxy-α,α-dideutero-N,N-di(trideuteromethyl)tryptamine and 5-methoxy-α,α,β,β-tetradeutero-N,N-di(trideuteromethyl)tryptamine.

In some embodiments, the salt is of an optionally substituted dimethyltryptamine compound and an acid selected from the group consisting of fumaric acid, tartaric acid, citric acid, acetic acid, lactic acid and gluconic acid, typically fumaric acid.

Accordingly, the salt may comprise:

any one or a combination of N,N-dimethyltryptamine, α-monodeutero-N,N-dimethyltryptamine, α,α-dideutero-N,N-dimethyltryptamine, α,β-dideutero-N,N-dimethyltryptamine, α,α,β-trideutero-N,N-dimethyltryptamine, α,β,β-trideutero-N,N-dimethyltryptamine, α,α,β,β-tetradeutero-N,N-dimethyltryptamine, N,N-di(trideuteromethyl)tryptamine ($d_6$-DMT) and α,α-dideutero-N,N-di(trideuteromethyl)tryptamine ($d_8$-DMT); or any one or a combination of 4-acetoxy-N,N-dimethyltryptamine, 4-acetoxy-α-monodeutero-N,N-dimethyltryptamine, 4-acetoxy-α,α-dideutero-N,N-dimethyltryptamine, 4-acetoxy-N,N-di(trideuteromethyl)tryptamine, 4-acetoxy-α,α-dideutero-N,N-di(trideuteromethyl)tryptamine, and 4-acetoxy-α,α,β,β-tetradeutero-N,N-di(trideuteromethyl)tryptamine; or any one or a combination of 5-methoxy-N,N-dimethyltryptamine, 5-methoxy-α-monodeutero-N,N-dimethyltryptamine, 5-methoxy-α,α-dideutero-N,N-dimethyltryptamine. 5-methoxy-N,N-di(trideuteromethyl)tryptamine, 5-methoxy-α,α-dideutero-N,N-di(trideuteromethyl)tryptamine, and 5-methoxy-α,α,β,β-tetradeutero-N,N-di(trideuteromethyl)tryptamine; or any one or a combination of 4-monohydrogen phosphate-N,N-dimethyltryptamine, 4-monohydrogen phosphate-α-monodeutero-N,N-dimethyltryptamine, 4-monohydrogen phosphate-α,α-dideutero-N,N-dimethyltryptamine. 4-monohydrogen phosphate-N,N-di(trideuteromethyl)tryptamine, 4-monohydrogen phosphate-α,α-dideutero-N,N-di(trideuteromethyl)tryptamine, and 4-monohydrogen phosphate-α,α,β,β-tetradeutero-N,N-di(trideuteromethyl)tryptamine; and an acid selected from the group consisting of fumaric acid, tartaric acid, citric acid, acetic acid, lactic acid and gluconic acid, typically fumaric acid.

In some embodiments, the salt is dimethyltryptamine fumarate, i.e. it comprises dimethyltryptamine as the optionally substituted dimethyltryptamine compound and fumaric acid.

The dimethyltryptamine compound (herein used interchangeably with optionally substituted dimethyltryptamine compound) may have a purity of about 80 to 100%. Sometimes, the purity is about 90 to 100%, such as from about 95 to 100%. Typically, the dimethyltryptamine compound has a purity of from about 99 to 100%, i.e. a purity greater than or equal to 99%. Percentages of purity herein are as determined by HPLC.

It is particularly advantageous to prepare the formulations of the present invention with a drug substance comprising the optionally substituted dimethyltryptamine compound or salt thereof with a purity of greater than 99%. By drug substance is meant, as is understood in the art, an active ingredient intended to furnish pharmacological activity or other direct effect in the diagnosis, cure, mitigation, treatment, or prevention of disease or to affect the structure or any function of the patient concerned, but does not include intermediates used in the synthesis of such ingredient. It will be understood that the drug substance may comprise one or more such active ingredients.

Preferred embodiments of any aspect of the present invention comprise a drug substance comprising an optionally substituted dimethyltryptamine compound or salt thereof having a purity of greater than or equal to 99% when measured by HPLC. Particularly preferred embodiments comprise a drug substance comprising an optionally substituted dimethyltryptamine compound or salt thereof having a purity of greater than or equal to 99.5%, even more preferably 99.7%, and even more preferably 99.9%, when measured by HPLC.

The concentration of the salt of the optionally substituted dimethyltryptamine compound within the formulation may be any desired concentration to achieve greater than or equal to 10 mg/ml freebase-equivalent, provided that the osmolality of the formulation is from about 250 to about 350 mOsm/Kg. The dimethyltryptamine compound may be at a concentration of greater than 20 mg/mL. A concentration of 28 mg/mL of dimethyltryptamine provides approximately 148 mOsm/kg (approximately 296 mOsm/kg with counterions taken into account). This allows for the provision of a further 54 mOsm/kg by other components of the formulation, such as the optional buffer. The salt of the dimethyltryptamine compound may be at a concentration of greater than 20 mg/mL, greater than 25 mg/mL, greater than 30 mg/mL, greater than 40 mg/mL, greater than 50 mg/mL, greater than 60 mg/mL or greater than 70 mg/m (as the freebase equivalent). Additionally, or alternatively, the optionally substituted dimethyltryptamine compound may be at a concentration of from about 10 mg/ml to about 150 mg/ml, from about 10 mg/ml to about 100 mg/ml, from about 10 mg/ml to about 80 mg/ml, from about 15 mg/ml to about 70 mg/ml, from about 15 mg/ml to about 50 mg/ml, or from about 20 mg/ml to about 40 mg/ml (as freebase equivalent). Typically, the optionally substituted dimethyltryptamine compound may be at a concentration of about 25 mg/ml (as freebase equivalent).

The total dose of the salt of the optionally substituted dimethyltryptamine compound to be used in any of the fourth to sixth aspects of the invention is suitably 10 mg to about 150 mg, preferably from about 10 mg to about 120 mg, preferably from about 10 mg to about 100 mg, preferably from about 10 mg to about 80 mg.

As described above, the formulation of the invention has an osmolality of from about 250 to about 350 mOsm/Kg. In some embodiments of the invention, the osmolality of the formulation is from about 250 to about 400 mOsm/Kg. In some embodiments, the osmolality of the formulation of the invention is from about 275 to about 325 mOsm/Kg, such as from about 280 to about 310 mOsm/Kg. Typically, the osmolality of the formulation is from about 295 to about 305 mOsm/Kg.

Sometimes, the concentration of optionally substituted dimethyltryptamine salt and optional buffer in the formulation gives rise to the desired osmolality. Alternatively, the desired osmolality may be achieved by inclusion of one or more tonicity agents in the formulation. Thus, in some embodiments, the formulation further comprises a tonicity agent. A tonicity agent is defined herein as a chemical that, on inclusion within a formulation, increases the osmolality of the formulation. As described above, the osmolality is the number of osmotically active particles (the number of solute particles) in 1 kg of a solution. Thus, a chemical that acts as a solute when incorporated into the formulation lies within the definition of a tonicity agent.

If the formulation further comprises a tonicity agent, the concentration of tonicity agent depends on the concentration of other components within the formulation, such as the optionally substituted dimethyltryptamine and buffer. For example, where the formulation without tonicity agent has an osmolality of about 60 mOsm/kg, at least about 190 mOsm/kg would be provided by a tonicity agent (e.g. 95 mM of sodium chloride). M. F. Powell, T. Nguyen and L. Baloian provide a review of excipients suitable for parenteral administration (administration other than by the mouth or alimentary canal) in *PDA J. Pharm. Sci. Technol.*, 52, 238-311 (1998). All soluble excipients listed in this review article that can be given by the intravenous route will, when added to the formulation, contribute to the osmolality and thus can be considered tonicity agents.

Suitable excipients for use in the formulations of the invention may be selected from the group consisting of ethanol, citric acid, trisodium citrate, benzalkonium chloride, microcrystalline cellulose, carboxymethylcellulose sodium, chlorobutanol, edetate disodium, glycerin, hydrochloric acid, methylparaben, polyethylene glycol, propylene glycol, propylparaben, saccharin sodium, sodium bicarbonate, sodium bisulphate, sodium bisulphite, sodium chloride, sodium hydroxide, sodium metabisulphite, sodium phosphate, sodium citrate, sulphuric acid, trisodium citrate, tromethamine, and mixtures thereof.

Some excipients may act as a cosolvent. Suitable solvents or cosolvents for use in the formulations of the invention may be selected from ethanol, polyethylene glycol, propylene glycol, and mixtures thereof. In some embodiments, the formulation comprises a cosolvent. In some embodiments, the formulation does not comprise a cosolvent. In particular, when the salt of the optionally substituted dimethyltryptamine compound is a fumarate, for example N,N-dimethyltryptamine fumarate or α,α-dideutero-N,N-dimethyltryptamine fumarate, the formulation does not comprise a cosolvent.

Suitable buffers for use in the formulations of the invention may be selected from the group consisting of phosphoric acid, citric acid, acetic acid, sodium phosphate, sodium citrate, sodium acetate, and mixtures thereof.

It will be understood that some excipients may have more than one function. For example, citric acid may be utilised as a buffer component, a flavouring agent, or as an antioxidant. A pH adjuster, for example hydrochloric acid, may also function as a tonicity agent.

In some embodiments, the tonicity agent is any one or a combination selected from the group consisting of dextrose, sodium chloride; phosphoric acid; a phosphate salt such as sodium phosphate or potassium phosphate; acetic acid; ethanol; citric acid; a citrate salt such as sodium citrate or potassium citrate; arginine; edetic acid; an edetate salt such as sodium edetate or calcium edetate; propylene glycol; sodium bicarbonate; sodium hydroxide; and hydrochloric acid.

Some of the tonicity agents listed above may be used to buffer the formulation (e.g. acetate salt, acetic acid, citrate salt, citric acid, phosphate salt, phosphoric acid). For the avoidance of doubt, where one of the tonicity agents listed above is used as the buffer, it is not also the defined tonicity agent, i.e. where the formulation further comprises a tonicity agent, the tonicity agent is different from the buffer. Typically, the tonicity agent is sodium chloride or dextrose.

In some embodiments, the formulation comprises the tonicity agent, such as sodium chloride, at a concentration of from about 120 mM to about 140 mM, such as from about 125 mM to about 135 mM. Sometimes, the concentration of the tonicity agent, such as sodium chloride, within the formulation is about 130 mM.

In some embodiments, the formulation consists essentially of the optionally substituted dimethyltryptamine salt, water, a base agent, optionally a buffer, and optionally a tonicity agent and/or pH adjuster. By this is meant, for example, that the presence of additional components within the formulation is permitted, provided the amounts of such additional components do not materially affect, in a detrimental manner, the essential characteristics of the formulation. Given that the intention behind including the optionally substituted dimethyltryptamine salt, water, the base agent, the optional buffer and the optional tonicity agent and/or pH adjuster in the formulation is to produce a pharmaceutical formulation of optionally substituted dimethyltryptamine which is suitable for both intramuscular injection and nebuliser inhalation, and which is stable for at least several weeks when stored, it will be understood that the inclusion of components that materially affect, in a detrimental manner, the stability of the formulation or its suitability for injection (e.g. its osmolality or pH), are excluded from the formulation. On the other hand, it will be understood that the presence of any components that do not materially affect, in a detrimental manner, the stability of the formulation or its suitability for injection, is included. Such components include anti-oxidants and antimicrobial preservatives. For an overview of pharmaceutical excipients and their properties, including those with anti-oxidant and antimicrobial properties, see P. J. Sheskey, W G Cook and C G Cable, *Handbook of Pharmaceutical Excipients*, Eighth Edition, Pharmaceutical Press, London 2017.

The base agent adjusts the pH of the formulation to the required pH range, for example from pH 5 to pH 6. The pH of a formulation including the optionally substituted dimethyltryptamine salt, water, and a buffer is often low, e.g. less than pH 5, and so a pH adjustment with a base agent may be required. The skilled person is able to asses suitable base agents to adjust the pH of the solution without risk of degradation of the optionally substituted dimethyltryptamine salt. The base agent may be sodium hydroxide or potassium hydroxide.

In some embodiments, the formulation further comprises an anti-oxidant. Suitable anti-oxidants commonly for use in the formulations of the invention include citric acid, sodium metabisulphite and mixtures thereof.

In some embodiments, the formulation further comprises an antimicrobial preservative. Suitable antimicrobial preservatives for use in the formulations of the invention include propylparaben (n-propyl parahydroxybenzoate), benzalkonium chloride and mixtures thereof.

Preferably, the formulation has an oxygen content of less than 5 ppm, preferably less than 2 ppm, such as between 0.1 ppm and 2 ppm. The skilled person is able to determine the oxygen content of the formulation using any technique known in the art to be suitable, such as using a dissolved oxygen meter (e.g. a Jenway 970 Enterprise Dissolved Oxygen Meter, available from Keison Products: http://www.keison.co.uk/products/jenway/970.pdf).

The formulation may be stored in any suitable container. In some embodiments the container may have a volume of 10 ml or less, 5 ml or less, 4 ml or less, 2 ml or less, 1 ml or less, or 0.5 ml or less. In some embodiments, to ameliorate degradation of the formulation further, the formulation is stored in a container adapted to prevent penetration of ultraviolet light, such as amber glass vial. In others, the container within which the formulation is stored is not so adapted (and may be, for example, made of clear glass) with protection against ultraviolet light, if desired, provided by secondary packaging (for example packaging within which the receptacle containing the formulation may be placed). Often, the container is airtight and the formulation is stored under an inert atmosphere, such as under nitrogen or argon, typically nitrogen. The formulation may be stored at room temperature, e.g. at about 20 to about 30° C. or at cooler temperatures, for example at about 2 to about 8° C. Alternatively, to ameliorate degradation of the formulation further, it may be stored in a freezer.

Preferably, the formulation is sparged with an inert gas, such as nitrogen or argon, to reduce the oxygen content of the formulation.

Viewed from a second aspect, the invention provides a kit suitable for preparing a formulation of the first aspect, said kit comprising a salt of an optionally substituted dimethyltryptamine compound; a base agent, optionally a buffer, which is separate to the salt; and optionally a tonicity agent and/or pH adjuster. In preferred embodiments of the second aspect of the present invention, the kit comprises an effective dose of an optionally substituted dimethyltryptamine compound for use in pharmacological-assisted psychotherapy (psychedelic assisted therapy) within a volume of 5 ml or less, preferably within a volume of 4 ml or less, 3 ml or less, 2.5 ml or less, 2 ml or less, 1 ml or less, or 0.5 ml or less.

Also provided is a kit to generate a formulation of the first aspect, the kit comprising:
   a first composition comprising a salt of an optionally substituted dimethyltryptamine compound; and
   a second composition comprising a base agent and optionally a buffer which is separate to the salt, and/or a tonicity agent, and or a pH adjuster,
   wherein the first and second compositions are mixed with water, and the resulting mixture generates the formulation of the first aspect.

For the avoidance of doubt, embodiments related to the optionally substituted dimethyltryptamine salt and the buffer as well as other features and embodiments of the first aspect of the invention as defined herein apply mutatis mutandis to the second aspect. For example, the optionally substituted dimethyltryptamine salt of the kit may comprise a Brønsted acid having a pKa at 25° C. of from about 3 to about 5, and a compound of Formula IA or Formula IB and/or the buffer may comprise an acetate salt and acetic acid.

The optionally substituted dimethyltryptamine salt within the kit may be a solid, e.g. in a powder or crystalline form. To ameliorate degradation of the optionally substituted dimethyltryptamine salt in the solid form, the salt may be lyophilised (freeze-dried) before incorporation into the kit. Lyophilising the salt comprises freezing it in the presence of solvent (typically water) and separating the solvent from the salt by sublimation.

When the kit further comprises a tonicity agent, the embodiments related to the optional tonicity agent of the first aspect of the invention as defined herein apply mutatis mutandis to the second aspect. For example, the tonicity agent may be any one or a combination selected from the group listed above.

Viewed from a third aspect, the invention provides a method of preparing a pharmaceutical formulation of the first aspect. The method comprises contacting the optionally substituted dimethyltryptamine salt, a base agent, optionally a buffer, and optionally a tonicity agent and/or pH adjuster, with water. In preferred embodiments of the third aspect of the present invention, the optionally substituted dimethyltryptamine salt comprises an effective dose of an optionally substituted dimethyltryptamine compound for use in pharmacological-assisted psychotherapy (psychedelic assisted therapy) within a volume of 5 ml or less, preferably within a volume of 4 ml or less, 3 ml or less, 2.5 ml or less, 2 ml or less, 1 ml or less, or 0.5 ml or less. For the avoidance of doubt, the embodiments of the first aspect of the invention apply mutatis mutandis to the third aspect. For example, the salt may be dimethyltryptamine fumarate; the buffer may comprise acetic acid and an acetate salt or phosphoric acid and a phosphate salt; and the tonicity agent may comprise sodium chloride.

It will be understood that the contacting of the method may be achieved in a variety of ways. Often, the optionally substituted dimethyltryptamine salt is dissolved in water to form a first solution to which the base agent and optional buffer are added and dissolved, forming a second solution. If a tonicity agent or pH adjuster is used, it is often added to and dissolved in the second solution. An additional solvent or cosolvent may be added to the first solution or second solution.

In some embodiments, an aqueous solution of the buffer is contacted with the salt, wherein the aqueous solution of the buffer has a pH of from about 5 to about 6.5, such as a pH from about 5 to about 6, or from about 5.3 to about 6, or from about 5.5 to about 6. In some embodiments, the aqueous solution of the buffer may have a pH of from 5 to 6. In some embodiments, the aqueous solution of the buffer has a pH of about 5.5 or about 6.

The optionally substituted dimethyltryptamine salt within the formulation may be formed by contacting optionally substituted dimethyltryptamine as a free base with an aqueous solution comprising a quantity of buffer suitable to stabilise the pH and act as counterion to the optionally substituted dimethyltryptamine when protonated.

Accordingly, the method of the invention may comprise contacting the optionally substituted dimethyltryptamine in free base form with a buffer, water and optionally a tonicity agent.

The method further comprises using a base agent to adjust the pH of the solution resultant from the contacting. Since the pH of the solution resultant from the contacting step is usually low, a subsequent pH adjustment step is required. pH adjustment often comprises contacting the solution with a suitable base agent, for example a strong base agent. The skilled person is able to assess which bases are suitable to adjust the pH of the solution resultant from the contacting without risk of degradation of the optionally substituted dimethyltryptamine salt. The pH of the solution resultant from the contacting is adjusted with a base agent which may be a suitable alkali, preferably sodium hydroxide or potassium hydroxide.

In some embodiments, the pH is further adjusted with a pH adjuster in order to achieve the desired pH. The pH adjuster may be a suitable acid, such as an acid selected from acetic acid, aspartic acid, benzene sulphonic acid, benzoic acid, citric acid, hydrochloric acid, hydrobromic acid, methane sulphonic acid, propionic acid, tartaric acid, fumaric acid, lactic acid, phosphoric acid, maleic acid, and sulphuric acid, or mixtures thereof. Preferably, the pH adjuster is selected from acetic acid, aspartic acid, benzene sulphonic acid, benzoic acid, citric acid, hydrochloric acid, hydrobromic acid, methane sulphonic acid, tartaric acid, fumaric acid, maleic acid, and sulphuric acid, or mixtures thereof. Preferably, the formulations of the invention comprise a pH adjuster which is hydrochloric acid.

As described above, to ameliorate degradation of the formulation further, it may be desirable to minimise the total oxygen content within the container in which the formulation is stored, the oxygen within the container equilibrating between the formulation and the headspace (if any) within the container. Accordingly, it may be desirable to store the formulation under an inert atmosphere for example by purging the headspace to reduce its oxygen content from about 20% typically found in air, to less than, for example, 1% or less than 0.5%. Additionally, or alternatively, in some embodiments, the method further comprises sparging the solution resultant from the contacting with an inert gas, such as nitrogen or argon, typically nitrogen.

As described above, dimethyltryptamine has a possible therapeutic role in the treatment of depression, obsessive-compulsive disorder, and substance abuse disorders (S. A. Barker, 2018, supra). Viewed from a fourth aspect, therefore, the invention provides a formulation of the first aspect or the kit of the second aspect for use as a medicament, or for use in combination with psychotherapy. In preferred embodiments of the fourth aspect of the present invention, the formulation comprises an effective dose of an optionally substituted dimethyltryptamine compound for use in pharmacological-assisted psychotherapy, or psychedelic assisted therapy, within a volume of 5 ml or less, preferably within a volume of 4 ml or less, 3 ml or less, 2.5 ml or less, 2 ml or less, 1 ml or less, or 0.5 ml or less.

Viewed from a fifth aspect, the invention provides a formulation of the first aspect or a kit of the second aspect for use in a method of treating a psychiatric or neurological disorder in a patient. In preferred embodiments of the fifth aspect of the present invention, the formulation comprises an effective dose of an optionally substituted dimethyltryptamine compound for use in pharmacological-assisted psychotherapy or psychedelic assisted therapy within a volume of 5 ml or less, preferably within a volume of 4 ml or less, 3 ml or less, 2.5 ml or less, 2 ml or less, 1 ml or less, or 0.5 ml or less.

Often, the psychiatric or neurological disorder is selected from the group consisting of (i) an obsessive compulsive disorder, (ii) a depressive disorder, (iii) an anxiety disorder, (iv) substance abuse and gambling disorders and (v) an avolition disorder. Often, the disorder is selected from the group consisting of major depressive disorder, treatment resistant major depressive disorder, post-partum depression, an obsessive compulsive disorder and an eating disorder such as a compulsive eating disorder.

Viewed from a sixth aspect, the invention provides a method of treating a psychiatric or neurological disorder comprising administering to a patient in need thereof a formulation of the first aspect. In preferred embodiments of the sixth aspect of the present invention, the formulation comprises an effective dose of an optionally substituted dimethyltryptamine compound for use in pharmacological-assisted psychotherapy or psychedelic assisted therapy within a volume of 5 ml or less, preferably within a volume of 4 ml or less, 3 ml or less, 2.5 ml or less, 2 ml or less, 1 ml or less, or 0.5 ml or less. The psychiatric or neurological disorder may be any of those described in relation to the fifth aspect. For example, the disorder may be selected from the group consisting of major depressive disorder, treatment resistant major depressive disorder, post-partum depression, an obsessive compulsive disorder and an eating disorder such as a compulsive eating disorder.

In the sixth aspect of the invention, the formulation of the first aspect may be administered in combination with psychotherapy (i.e. in pharmacological-assisted psychotherapy).

In order to treat the disorder, the formulation comprises an effective amount of the dimethyltryptamine compound, i.e. an amount that is sufficient to reduce or halt the rate of progression of the disorder, or to ameliorate or cure the disorder and thus produce the desired therapeutic or inhibitory effect.

The formulation is suitable for intramuscular injection, thus its administration to a patient typically comprises injection of the formulation.

The formulation may be suitable for bolus injection, in which a discrete amount of an optionally substituted dimethyltryptamine salt is administered in one injection such that the concentration of optionally substituted dimethyltryptamine in the body quickly increases.

Typically, IM injections administer a dosage volume of 5 ml or less, using a 19-27 needle gauge, more typically a 20-25 needle gauge. The concentrated formulations of the present invention, allow the administration of lower volumes, using a higher needle gauge, suitable 22-27, which may reduce pain associated with injection. The injection volume may be from about 0.5 to about 4 ml, from about 0.5 to about 3 ml, or from about 0.5 to about 2.5 ml.

The formulation is also suitable for nebulised inhalation, thus its administration to a patient may comprise inhalation of the formulation using a nebuliser.

When the formulations of the invention comprise deuterated N,N-dimethyltryptamine compounds, for example α,α-dideutero-N,N-dimethyltryptamine ($d_2$-DMT), α,α,β,β-tetradeutero-N,N-dimethyltryptamine ($d_4$-DMT), N,N-di(trideuteromethyl)tryptamine ($d_6$-DMT), α,α-dideutero-N,N-di(trideuteromethyl)tryptamine ($d_8$-DMT), and α,α,β,β-tetradeutero-N,N-di(trideuteromethyl)tryptamine ($d_{10}$-DMT), a lower dose may be effective, rendering the formulation of the invention particularly suitable for lower dose volumes. This has the advantage of allowing the IM formulations to be administered at a wider range of injection sites. The higher concentrations and lower dose volumes of the present formulations may also enable the use of a wide range of nebuliser equipment and may allow shorter inhalation times.

In a tenth aspect, the invention provides a lyophilised powder formulation comprising a formulation as defined in the first aspect of the invention which has been lyophilised (i.e. freeze dried).

Lyophilisation (also known as freeze drying or cryodesiccation) is a drying process carried out at low temperature. Lyophilisation generally involves reducing temperature and pressure to below the substance's triple point and removing the frozen solvent (e.g. water ice) by sublimation. For aqueous compositions, such as those disclosed herein, lyophilisation may be carried out at temperatures of from about −50° C. to −80° C., preferably about −70° C., and pressures of from about 1000 Pa (0.01 bar) to about 100 Pa (0.001 bar), preferably about 800 Pa (0.008 bar).

In an eleventh aspect, the invention provides a method of preparing a lyophilised powder formulation as defined in the tenth aspect, comprising drying the formulation as defined in the first aspect of the invention by lyophilisation.

In a twelfth aspect, the invention provides a method of preparing an aqueous formulation comprising mixing the lyophilised powder formulation as defined in the tenth aspect or as prepared in the method of the eleventh aspect into water to provide a formulation comprising the salt of an optionally substituted dimethyltryptamine compound, the buffer which is separate to the salt, the base agent and water to provide a formulation having a pH of from about 5 to about 6.5, a concentration of about 10 mg/ml as freebase or greater, and an osmolality of from about 250 to about 350 mOsm/Kg. The formulation may have a pH of from about 5 to about 6, or a pH of from 5 to 6. For the avoidance of doubt, embodiments of the first aspect of the invention apply mutatis mutandis to the tenth, eleventh and twelfth aspects of the invention.

For the avoidance of doubt, embodiments related to each aspect of the invention apply mutatis mutandis to the other aspects of the invention. Each and every reference referred to herein is hereby incorporated by reference in its entirety, as if the entire content of each reference was set forth herein in its entirety.

The entire contents of PCT/EP2021/073189, UK patent application number 2119021.0 and U.S. patent application Ser. No. 17/574,424, and any validly claimed priority documents are incorporated herein by reference.

Synthesis of the compounds for use in the formulations of the invention may be carried out according to the schemes and examples described in WO 2020/245133 A1, WO 2021/116503 and WO 2021/089873 A1 (all Small Pharma Ltd). For deuterated compounds, the extent of deuteration was determined according to the method described in WO 2020/245133 A1, WO 2021/116503 and WO 2021/089873 A1.

EXAMPLES

Example 1: N,N-Dimethyltryptamine

N,N-DMT 220.9 g (as free base) was prepared as N,N-DMT fumarate, using the chemistry disclosed in Scheme 2 and the Examples section of WO 2021/089873. An additional 4-6 g of six partially deuterated mixtures were also produced using modified conditions.

Example 2: Deuterated N,N-Dimethyltryptamine

Synthesis of Deuterated Mixtures of DMT Compounds

A modified synthesis using solid $LiAlH_4/LiAlD_4$ mixtures was adopted, using 1.8 equivalents of $LiAlH_4/LiAlD_4$ versus 0.9 equivalents of $LiAlH_4$ using the process described above for N,N-Dimethyltryptamine, as disclosed in WO 2021/089873. The deuterated dimethyltryptamine compounds include α-protio,α-deutero-dimethyltryptamine and α,α-dideutero-dimethyltryptamine.

The data for the six deuterated reactions are tabulated in the table below:

| Mixture No. ($LiAlH_4:LiAlD_4$ ratio) | Input (stage 1) | Output stage 3 (yield) | Purity by HPLC | Purity by NMR | Deuteration % | | |
|---|---|---|---|---|---|---|---|
| | | | | | $D_0$ | $D_1$ | $D_2$ |
| 1 (0:1) | 5 g | 5.3 g (65%) | 99.7% | >95% | 0.7% | 2.7% | 96.6% |
| 2 (1:1) | 6 g | 5.699 g (63%) | 99.9% | >95% | 30.0% | 48.3% | 21.7% |
| 3 (1:2) | 5 g | 4.206 g (52%) | 99.9% | >95% | 16.5% | 46.8% | 36.8% |
| 4 (1:3) | 5 g | 5.558 g (68%) | 99.8% | >95% | 9.3% | 41.5% | 49.2% |
| 5 (2:1) | 5 g | 4.218 g (52%) | 99.9% | >95% | 47.5% | 41.3% | 11.2% |
| 6 (3:1) | 5 g | 5.0 g (62%) | 99.4% | >95% | 57.5% | 35.3% | 7.4% |

5- and 4-Substituted dimethyltryptamine and deuterated dimethyltryptamine compounds may be prepared by analogous processes, using the appropriate starting materials. To synthesise 5-methoxy-N,N-dimethyltryptamine or 4-methoxy-N,N-dimethyltryptamine, 3-indoleacetic acid may be replaced with 5-methoxyindole-3-acetic acid (see synthesis of α,α-dideutero-5-methoxydimethyltryptamine described below) or 4-methoxyindole-3-acetic acid respectively, both of which are commercially available (for 5-methoxyindole-3-acetic acid, for example from Sigma-Aldrich (code M14935-1G), for 4-methoxyindole-3-acetic acid see for example Aaron chemicals (code AR00VTP1)).

5-Methoxy-N,N-dimethyltryptamine (see Sigma-Aldrich code M-168-1ML), 4-methoxy-N,N-dimethyltryptamine (see Cayman Chemical code 9000895), 4-acetoxy-N,N-dimethyltryptamine (see Cayman Chemical code 14056) and 3-[2-(Dimethylamino)ethyl]-1H-indol-4-yl phosphate (psilocybin, see Sigma-Aldrich CAS Number 520-52-5) are also commercially available.

Example 3: α,α-dideutero-5-methoxydimethyltryptamine

Synthesis of α,α-dideutero-5-methoxydimethyltryptamine
Stage 1:
To a 100 mL 3-neck flask under $N_2$ was charged 5-methoxyindole-3-acetic acid (3.978 g, 19.385 mmol), HOBt (~20% wet) (3.927 g, 23.261 mmol) and DCM (40 mL). EDC.HCl (4.459 g, 23.261 mmol) was then charged in portions over 15 minutes at <30° C. The reaction mixture was stirred at ambient temperature for 1 hour before being charged with 2 M dimethylamine (14.54 mL, 29.078 mmol) dropwise over 15 minutes at <25° C. After stirring for 1 hour, HPLC indicated no SM remained. The reaction mixture was then charged with 10% $K_2CO_3$ (20 mL), stirred for 5 minutes then allowed to separate. The lower aqueous layer was removed and back extracted with DCM (10 mL×2). The organic extracts were combined, washed with saturated brine (10 mL) then dried over $MgSO_4$ and filtered. The filtrate was concentrated in vacuo at 45° C. to provide 3.898 g active (yield=87%) of product in a purity of 95.7% by HPLC.

Stage 2:

To a 100 mL 3-neck flask under $N_2$ was charged Stage 1 methoxy derivative (3.85 g, 16.586 mmol) and THF (19.25 ml). 2.4 M $LiAlD_4$ in THF (6.22 mL, 14.927 mmol) was then charged dropwise over 30 minutes at <40° C. The reaction mixture was heated to 60° C. for 1 hour where HPLC indicated 0.1% SM remained. The reaction mixture was then cooled to ambient temperature and quenched into 25% Rochelle's salts (38.5 mL) dropwise over 30 minutes at <30° C. The resultant suspension was stirred for 1 hour before being allowed to separate. The lower aqueous layer was then removed, and the upper organic layer washed with saturated brine (9.6 mL). The organics were then dried over $MgSO_4$, filtered and concentrated in vacuo before being subjected to an azeotrope from EtOH (10 mL×2). This provided 3.196 g active (yield=88%) of product in a purity of 91.5% by HPLC.

Stage 3:

To a 50 mL 3-neck flask under $N_2$ was charged fumaric acid (1.675 g, 14.430 mmol) and a solution of Stage 2 methoxy derivative (3.15 g, 14.299 mmol) in EtOH (37.8 mL). The mixture was then heated to 75° C. for 1 hour, this did not produce a solution as expected, the mixture was further heated to reflux (78° C.) which still failed to provide a solution. The suspension was therefore cooled to 0-5° C., filtered and washed with EtOH (8 mL×2) before being dried at 50° C. overnight. This provided 3.165 g (yield=65%) of material in a purity of 99.9% by HPLC.

Further compounds for use in the formulations of the invention may be prepared according to the processes described in WO 2021/116503.

Example 4: $d_6$-Dimethyltryptamine

Synthesis of $d_6$-DMT

Stage 1

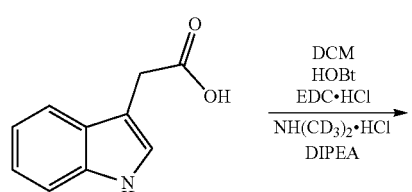

Molecular Weight: 175.18

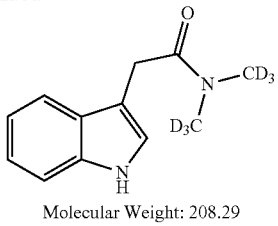

Molecular Weight: 208.29

EDC.HCl (15.7 g, 81.90 mmol) was added to 3-indoleacetic acid (12.0 g, 68.50 mmol) and HOBt.$H_2O$ (1.16 g, 75.75 mmol) in DCM (108 mL) at room temperature. The reaction was stirred for 1 hour after which N,N-diisopropylethylamine (DIPEA) (35.6 mL, 205.75 mmol) and $d_6$-dimethylamine.HCl (9.0 g, 102.76 mmol) were added (temperature maintained below 30° C.). The reaction was stirred for 1 hour at room temperature after which analysis by HPLC indicated 65.6% product with 28.9% 3-indoleacetic acid remaining. DIPEA (11.9 mL, 68.78 mmol) was added and the reaction was stirred for 1 hour at room temperature. HPLC indicated no change in conversion. Aqueous potassium carbonate (6.0 g in 54 mL water) was added and the phases were separated. The aqueous phase was extracted with DCM (2×30 mL). The combined organics were washed with brine (2×30 mL) then aqueous citric acid (20 w/w %, 50 mL), dried over $MgSO_4$ and filtered. The filtrate was stripped and the resulting solids were slurried in TBME (120 mL) and isolated by filtration. Purification by flash column chromatography yielded 8.34 g of the desired product (58% yield). $^1$H NMR confirmed the identity of the product.

Stage 2

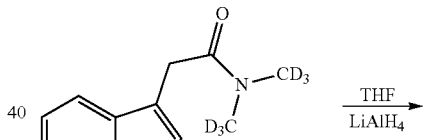

Molecular Weight: 208.29

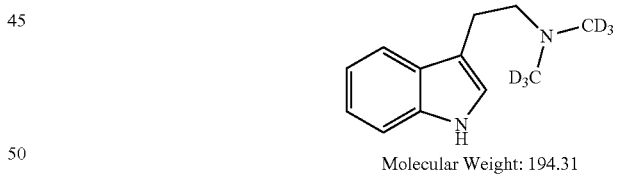

Molecular Weight: 194.31

$LiAlH_4$ (1 M in THF, 17.3 mL, 17.28 mmol) was added to a suspension of stage 1 (4.0 g, 19.20 mmol) in THF (10 mL) at <30° C. The resulting reaction was heated to 60-65° C. and stirred for 2 hours. HPLC analysis indicated complete consumption of stage 1 with 97.3% product formed. The reaction was cooled to room temperature and quenched into aqueous Rochelle's salts (10 g in 30 mL water) at <30° C. After stirring for 1 hour, the phases were separated. The aqueous phase was extracted with THF (20 mL). The combined organics were washed with brine (20 mL), dried over $MgSO_4$, filtered and stripped (azeotroped with ethanol, 20 mL) to give the desired product as an amber oil (3.97 g). $^1$H NMR confirmed the identity of the product and indicated 8.5% ethanol was present (no THF) giving an active yield of 3.63 g, 97%.

Stage 3

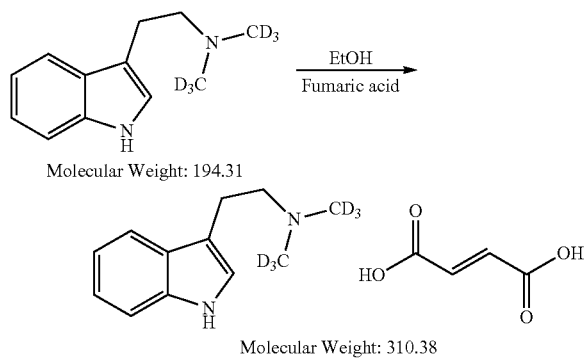

Molecular Weight: 194.31

Molecular Weight: 310.38

$d_6$-DMT free base (3.6 g active, 18.53 mmol) was dissolved in ethanol (43 mL) at room temperature. Fumaric acid (2.15 g, 18.53 mmol) was added and the solution was heated to 75° C. (solids crystallised during heating and did not re-dissolve). The resulting suspension was cooled to 0-5° C. and stirred for 1 hour. The solids were isolated by filtration, washed with ethanol (2×7 mL) and pulled dry. Further drying in a vacuum oven at 50° C. yielded the desired $d_6$-DMT fumaric acid salt (4.98 g, 87%).

Example 5: $d_8$-Dimethyltryptamine

Synthesis of $d_8$-DMT
Stage 1 (coupling of 3-indoleacetic acid and $d_6$-dimethylamine), was carried out according to the process described for Example 4, Stage 1 above
Stage 2

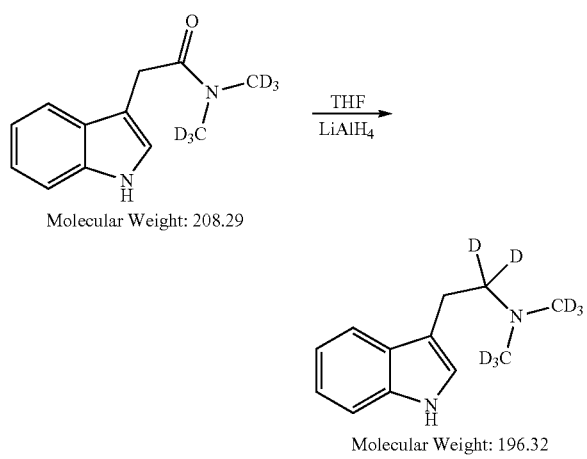

Molecular Weight: 208.29

Molecular Weight: 196.32

$LiAlD_4$ (1 M in THF, 17.3 mL, 17.28 mmol) was added to a suspension of the product of Stage 1 (4.0 g, 19.20 mmol) in THF (10 mL) at <30° C. The resulting reaction was heated to 60-65° C. and stirred for 2 hours. HPLC analysis indicated complete consumption of the stage 1 with 97.3% product formed. The reaction was cooled to room temperature and quenched into aqueous Rochelle's salts (10 g in 30 mL water) at <30° C. After stirring for 1 hour, the phases were separated. The aqueous phase was extracted with THF (20 mL). The combined organics were washed with brine (20 mL), dried over $MgSO_4$, filtered and stripped (azeotroped with ethanol, 20 mL) to give the desired product as an amber oil (4.01 g). $^1H$ NMR confirmed the identity of the product and indicated 8.6% ethanol was present (no THF) giving an active yield of 3.66 g, 97%.

Stage 3

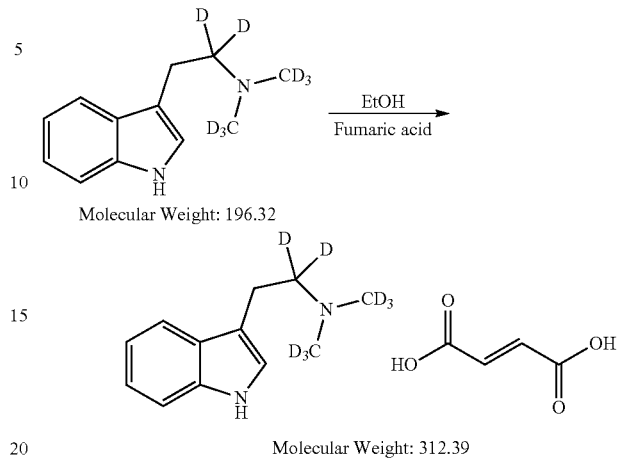

Molecular Weight: 196.32

Molecular Weight: 312.39

$d_8$-DMT free base (3.6 g active, 18.53 mmol) was dissolved in ethanol (43 mL) at room temperature. Fumaric acid (2.15 g, 18.53 mmol) was added and the solution was heated to 75° C. (solids crystallised during heating and did not re-dissolve). The resulting suspension was cooled to 0-5° C. and stirred for 1 hour. The solids were isolated by filtration, washed with ethanol (2×7 mL) and pulled dry. Further drying in a vacuum oven at 50° C. yielded the desired $d_8$-DMT fumaric acid salt (4.62 g, 81%).

Example 6: $d_6$-5-Methoxydimethyltryptamine

Synthesis of $d_6$-5-MeO-DMT
Stage 1
The coupling of 5-methoxy-3-indoleacetic acid and $d_6$-dimethylamine was carried out on a 20 g scale by a process analogous to that described for Stage 1 of Example 4 hereinabove. Purification by flash column chromatography yielded (87%) of a light brown solid, with 97.8% purity by HPLC. Molecular weight: 238.32.
Stage 2
The product of Example 6, Stage 1 was reacted with $LiAlH_4$ in THF according to the process described for Stage 2 of Example 4. The reaction was carried out on a 9 g scale to produce $d_6$-5-MeO-DMT as an amber oil with a yield of 8.22 g (7.40 g active, 87.3%) and 98.4% purity by HPLC. Molecular weight: 224.34
Stage 3
The fumarate salt of $d_6$-5-MeO-DMT was produced according to the process described for Stage 3 of Example 4. 6.04 g (65%) of an off-white solid was obtained with a purity of 99.61% by HPLC. NMR and XRPD data indicated the hemi-salt was isolated. Molecular weight: 564.74 (as hemi-salt)

Example 7: $d_8$-5-Methoxydimethyltryptamine

Synthesis of $d_8$-5-MeO-DMT
Stage 1
The coupling of 5-methoxy-3-indoleacetic acid and $d_6$-dimethylamine was carried out on a 20 g scale by a process analogous to that described for Stage 1 of Example 4 hereinabove. Purification by flash column chromatography yielded (87%) of a light brown solid, with 97.8% purity by HPLC. Molecular weight: 238.32.
Stage 2
The product of Example 7, Stage 1 was reacted with $LiAlD_4$ in THF on a 9 g scale according to the process described for Stage 2 of Example 5. Purification yielded 8.12 g (7.58 g active, 88.7%) of the product $d_8$-5-MeO-DMT as an amber oil, with 97.9% purity by HPLC. Molecular weight: 226.35

Stage 3

The fumarate salt of $d_8$-5-MeO-DMT was produced according to the process described for Stage 3 of Example 4. 9.6 g of the product $d_8$-5-MeO-DMT fumaric acid was obtained with 99.71% purity by HPLC. Molecular weight: 342.42.

Extent of Deuteration.

| Compound | Molecular Weight (free base equivalent) | D0 | D4 | D5 | D6 | D7 | D8 |
|---|---|---|---|---|---|---|---|
| $D_6$- DMT (Example 4) | 194.31 | N/D | LT 0.01% | 1.2% | 98.8% | | |
| $D_8$- DMT (Example 5) | 196.32 | N/D | | | 0.1% | 3.2% | 96.7% |
| $D_6$-MeO-DMT (Example 6) | 224.34 | N/D | | 0.4% | 99.6% | | |
| $D_8$-MeO-DMT (Example 7) | 226.35 | N/D | | | 3.9% | 3.2% | 92.8% |

Note:
N/D = not detectable;
LT = less than.

$D_6$-5-hydroxydimethyltryptamine and $d_8$-5-hydroxydimethyltryptamine may be prepared by a process analogous to that described for Examples 6 and 7 respectively, using 5-hydroxy-3-indoleacetic acid as a starting material. Alternatively, $d_6$-5-hydroxydimethyltryptamine and $d_8$-5-hydroxydimethyltryptamine may be prepared from $d_6$-5-methoxydimethyltryptamine and $d_8$-5-methoxydimethyltryptamine, respectively, by demethylation of the 5-methoxy group using standard procedures, e.g. $BBr_3$ demethylation.

Example 8: An In Vivo Investigation Pharmacokinetic (PK) Profile

An in vivo investigation of the pharmacokinetic (PK) profile of N,N-dimethyltryptamine (DMT, SPL026), α,α,-bis-deuterium-N,N-dimethyltryptamine ($d_2$-DMT, SPL028i) and α,α,bis-deuterio-N,N-hexadeuterio-dimnethyltryptamine ($d_8$-DMT, SPL028viii) following intramuscular (IM) dosing was performed in rats.

Test Compounds

| Compound | Chemical name | Molecular formula | Salt molecular weight | Freebase molecular weight |
|---|---|---|---|---|
| SPL026 | N,N-dimethyltryptamine (DMT) fumarate salt | $C_{12}H_{16}N_2$ | 304.34 | 188.27 |
| SPL028i | α,α,-bis-deuterium-N,N-dimethyltryptamine fumarate salt | $C_{12}H_{14}D_2N_2$ | 306.31 | 190.24 |
| SPL028viii | α,α,bis-deuterio-N,N-hexadeuterio-dimethyltryptamine fumarate salt | $C_{12}H_8D_8N_2$ | 312.35 | 196.32 |

Methods

12 Male (7-8 weeks old) Sprague Dawley rats (bodyweight 250-300 g) were dosed as follows:

| Route | Animals | Test compounds | Dose level (mg/kg) fumarate [freebase] |
|---|---|---|---|
| IM | 4 Male | SPL026; SPL028viii (cassette dose) | 3.5 [2.2] per compound |
| IM | 4 Male | SPL028i | 3.5 [2.2] |
| IM | 4 Male | SPL028i | 10 [6.2] |

Housing and Husbandry

| | |
|---|---|
| Environmental conditions | Temperature 21° C. ± 2° C. |
| | Relative humidity 45% to 65% |
| | Daily light cycle 12 h fluorescent lighting and 12 h dark |
| | Temperature and relative humidity will be continuously recorded |
| Equilibration period | Minimum period of 4 days prior to use |
| Housing | Grouped (up to 4) in polypropylene cages with solid floors |
| Identification | Unique number by tail marking with indelible ink |
| Health | A health examination will occur on receipt and the health status will be monitored throughout the acclimatization period. Any animals considered unhealthy will be excluded |

-continued

| | |
|---|---|
| | from the study. The suitability of each animal for experimental use will be confirmed before use |
| Diet | Name: RM1 (E) SQC pelleted diet<br>Supplier: Special Diets Services, Witham, Essex, UK<br>Availability: ad libitum<br>A diet analysis certificate for each batch used will be retained at Pharmaron UK Ltd. It is considered unlikely that any constituent of the diet will interfere with the study. Food will be available ad libitum for the duration of the study. |
| Drinking water: | Type: Domestic potable water.<br>Availability: ad libitum<br>The water quality will be in compliance with the Water Supply (UK) Regulations (2000). Routine chemical and bacterial analyses are conducted periodically by the local water authority. It is considered unlikely that any constituent of the water will interfere with the study. |

Dose Regimen

| Compound | SPL026 and SPL028viii | SPL028i | SPL028i |
|---|---|---|---|
| Route and frequency | Single Intramuscular | Single Intramuscular | Single Intramuscular |
| Dose level (mg/kg) (fumarate) | 3.5 mg/kg per compound | 3.5 | 10 |
| Dose volume (mL/kg) | 0.286 | 0.286 | 0.286 |
| Dose concentration (mg/mL) | 12.25 | 12.25 | 34.97 |
| Vehicle | Dissolve in saline | | |

A cassette dose of 3.5 mg/kg SPL026 fumarate and 3.5 mg/kg SPL028viii fumarate were administered as a single IM dose in 4 different male animals, to allow for a direct inter-animal comparison of SPL026 and SPL028viii and thereby, avoid confounding effects of inter-animal variability. 3.5 mg/kg and 10 mg/kg SPL028i fumarate were administered as a single IM dose in 4 different male animals.

Dosing Procedures

Animals were weighed the morning of dosing with doses being administered based on the bodyweight and the specified dose volume.

IM dosing apparatus consisted of an appropriately sized insulin syringe. Injection site were shaved the morning of dosing. During dosing, the dose was dispensed directly into the thigh muscle.

PK Sampling

Following dosing, serial whole blood samples (ca. 200 µL) will be collected into individual $K_2$EDTA treated containers from a lateral tail vein via an indwelling cannula. Samples were collected at the following times post dose:

IM Pre-dose, 5, 10, 25, 30, 45, 60, 90, 120, and 180 minutes

Blood samples were placed on a cooling block before being centrifuged at 10,000 g, 2 minutes at ca. 4° C. and the resultant plasma drawn off. All samples will be stored at ca. −80° C.

Bioanalysis

The bioanalysis of DMT, d8-DMT and d2-DMT in rat $K_2$EDTA plasma was performed using LC-MS/MS. The table below details the 2 methods that were qualified:

| Method Number | Calibration Standards & QC's prepared with | Internal Standard | Accurately Quantify |
|---|---|---|---|
| 1 | SPL026 (DMT) & SPL028viii ($d_8$-deuterated DMT) | SPL028vii ($d_6$-deuterated DMT) | SPL026 (DMT) & SPL028viii ($d_8$-deuterated DMT) |
| 2 | SPL028i ($d_2$-deuterated DMT) | SPL028vii ($d_6$-deuterated DMT) | SPL028i ($d_2$-deuterated DMT) |

Concentrations of DMT and $d_8$-DMT were quantified with a target Lower limit of Quantification (LLOQ) of ca 0.310 ng/mL of DMT, $d_8$-DMT and $d_2$-DMT using 20.0 µL of rat plasma and were qualified using the following methods:

Assay Linearity—A calibration curve prepared in duplicate containing ≥8 concentration levels as well as control blank and zero (IS only). Acceptance criteria—A minimum of 75% of the calibration standards (non-zero samples) must be ≤±20% relative error (RE) (≤±25% RE at the lower limit of quantitation) of their prepared nominal concentrations.

Sensitivity—Minimum signal to noise at LLOQ concentration must be 5:1.

Precision and Accuracy—a single analytical batch containing QCs at Low, Medium and High concentrations in replicate (n=6). Acceptance criteria—Intra-batch precision (CV) and accuracy (RE)≤20%.

Selectivity—The qualitatively assessment of chromatograms from control blank matrix from at least one source for the presence of potentially interfering peaks. Acceptance criteria—The response of any co-eluting interference must be ≤25% of the LLOQ calibration standard peak area. The response of any co-eluting interference must be less than 5% of the zero sample peak area for the internal standard.

Stability—Stability in matrix for QC Med in replicate (minimum n=3) will be assessed for at least 2 hours at the sample processing temperature for DMT only. Acceptance criteria—precision (CV) and accuracy (RE)≤20%.

Carryover—Assessed in at least one control blank matrix sample (carryover blank) analysed immediately after the upper limit of quantification (ULOQ) calibration standard. Acceptance criteria—Analyte carryover should be ≤25% of the analyte peak area in the LLOQ standard. Internal standard carryover should be ≤5% of the internal standard peak area in the LLOQ standard sample.

PK Parameters

Pharmacokinetic parameters of DMT (SPL026), $d_8$-DMT (SPL028viii) and $d_2$-DMT (SPL028i) in plasma were derived by non-compartmental analysis using the plasma concentration-time profile for each animal.

Results

The results are set out in FIG. 1. These data show that $d_8$-DMT (SPL028viii) and $d_2$-DMT (SPL028i) has a greater overall exposure when compared with DMT (SPL026) following IM dosing at 3.5 mg/kg.

Figure 1B:
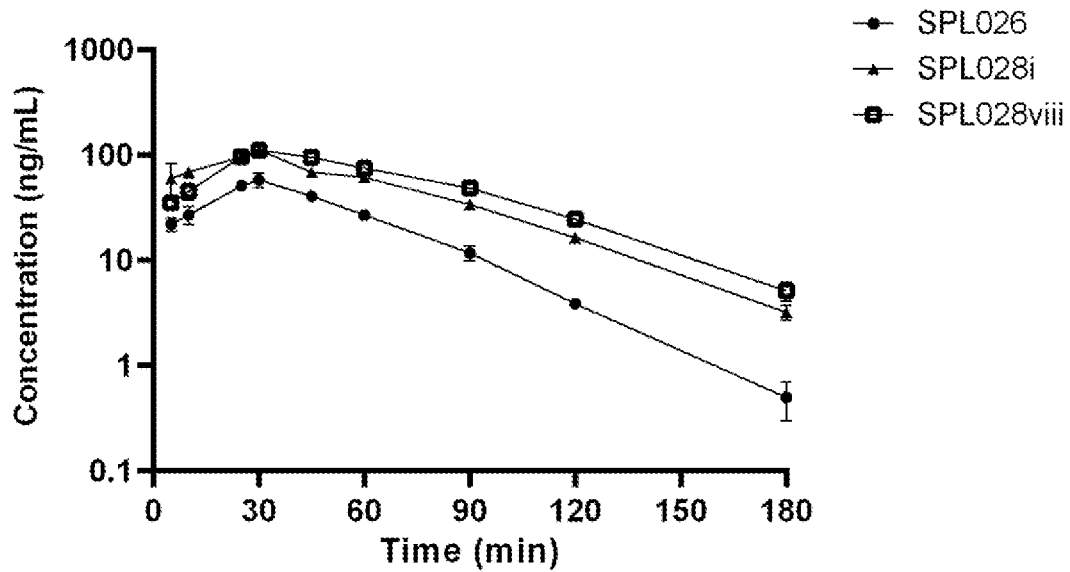
Figure 2A:
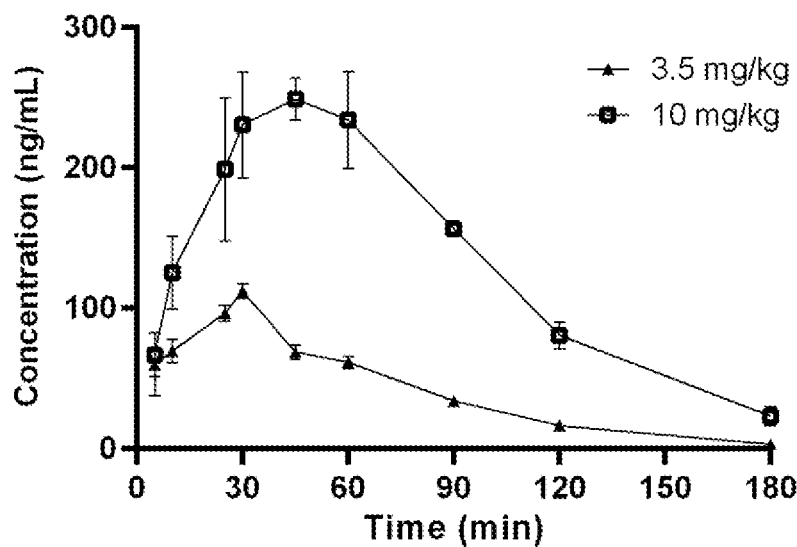
FIG. 2A and FIG. 2B show plots of the mean plasma d$_2$-DMT (SPL028i) concentration over time following 3.5 mg/kg and 10 mg/kg (as fumarate) IM doses in vivo.
Figure 2B:
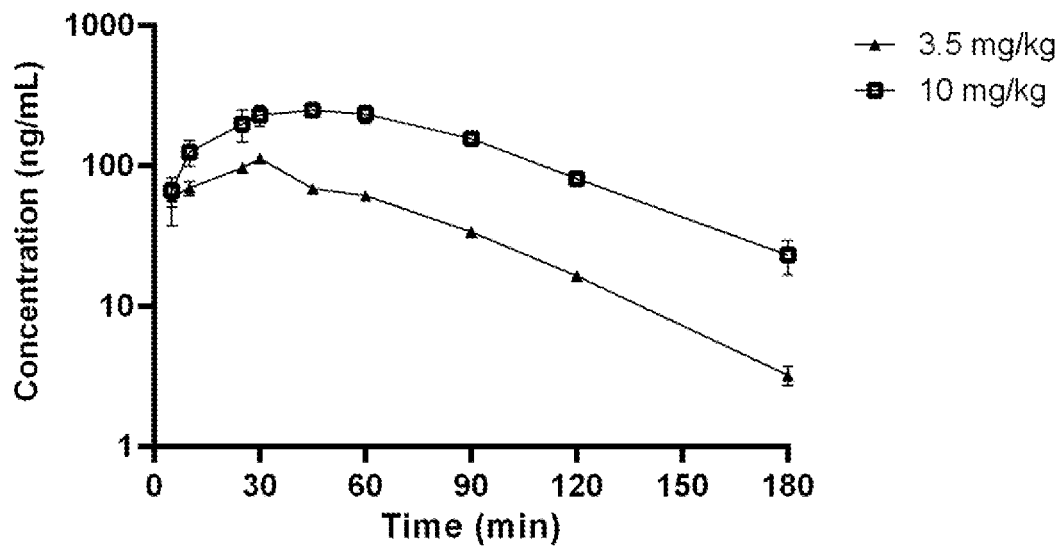

FIGS. 1A and 1B show linear and semi-log plots of the mean DMT (SPL026), $d_8$-DMT (SPL028viii) and $d_2$-DMT (SPL028i) concentration over time following 3.5 mg/kg fumarate IM dose (added as a cassette), in vivo. FIG. 1A—Linear plot, FIG. 1B—Semi-log plot, SEM error bars. FIGS. 2A and 2B shows linear and semi-log plots of the mean $d_2$-DMT (SPL028i) concentration over time following 3.5 mg/kg and 10 mg/kg fumarate IM doses in vivo. FIG. 2A—Linear plot, FIG. 2B—Semi-log plot, SEM error bars. An ANOVA with pairwise comparisons was performed to analyse the effect of dose group on PK parameters. There was a statistically significant difference in the mean area under curve from time 0 extrapolated to infinity ($AUC_{0-inf}$) between SPL026 and SPL028viii groups and between SPL026 and SPL028i groups following administration of equivalent IM doses to both groups, indicating that a significantly higher total systemic exposure of SPL028viii and SPL028i compared to SPL026 following single IM doses.

| $AUC_{0-inf}$ (min · ng/mL) | P value |
|---|---|
| SPL026 (3.5 mg/kg) vs. SPL028viii (3.5 mg/kg) | <0.001*** |
| SPL026 (3.5 mg/kg) vs. SPL028i (3.5 mg/kg) | <0.001*** |

Cmax was found to be significantly higher for $d_8$-DMT (SPL028viii) and $d_2$-DMT (SPL028i) when compared with DMT (SPL026) following IM dosing (p=0.005**).

There was a 144% increase in Cmax and 237% increase in $AUC_{0-inf}$ of $d_2$-DMT (SPL028i) at 10 mg/kg dose when compared to 3.5 mg/kg dose level. Dose response relationship level differences in Cmax and $AUC_{0-inf}$ were significantly different from each other (p<0.05* and p<0.001***, respectively) indicating a significant dose-response relationship.

The invention is further illustrated by the following embodiments.

Development of Formulation

All stated concentrations below are expressed in terms of the free base (i.e. in the absence of fumarate counterion). To do so, a correction factor of 1.59 has been applied to the specific batch of drug substance as supplied.

Experimental Details

The stability of a N,N-dimethyltryptamine (DMT) fumarate formulation was assessed at a concentration of 20 mg/mL and at a pH 4, 5, 6, 7, 8 and 9. A Britton-Robinson (B-R) buffer system (also known as a universal buffer) was used to vary the pH. A B-R buffer system typically consists of a mixture of 0.04 M boric acid, 0.04 M phosphoric acid and 0.04 M acetic acid and is titrated to the desired pH with 0.2 M sodium hydroxide. The system enables the pH to be varied while holding the osmolality constant.

Seven solutions, each containing a nominal concentration of 20 mg/mL of DMT fumarate were prepared in Britton-Robinson (B-R) buffer solution. On dissolution of DMT fumarate in each test formulation (DMT fumarate was very soluble, needing only swirling and shaking in each), the pH of each test formulation was then adjusted to pH 4, 5, 6, 7, 8 and 9 using sodium hydroxide solution.

Solubility of a concentration of 20 mg/mL of DMT fumarate was confirmed at pH 4, 5, 6 and 7—these solutions were clear and colourless. The sample at pH 8 was hazy and the samples at pH 9 and pH 10 contained a precipitate. Following overnight storage under ambient conditions, the pH of each solution was measured and the results showed no changes from the initial pH values. Each sample was then filtered and analysed for content. Each solution, including the high pH solutions where precipitate was present, contained approximately the same content of DMT fumarate.

pH Stability pH-stability of DMT fumarate at a nominal concentration of 2.5 mg/mL was assessed in 40 mM Britton-Robinson buffer solution over the buffer solution range pH 4 to 9 (nominal). The pH of each formulation was measured at preparation, following 7 days storage at 40° C. and then further storage over an additional 3 days at 40° C. and 7 days at 50° C. (so a total further storage of 10 days). Analysis of these formulations was performed on preparation, and then after 7 and 17 days storage for content (assay) and related substances.

Two extra aliquots of the pH 7 (nominal) solution were taken for additional testing, one was sparged with nitrogen and the second was stressed under intense UV light for 4 hours equivalent to 1 ICH unit (200 watt hours UVA, 0.6 million luxhours).

On preparation of each formulation, there was a drop in pH in the range of 0.14 units (pH 4 formulation) to 1.29 units (pH 9 formulation) this being due to the acidic nature of the drug substance. Once prepared, the pH of each formulation remained stable at the two subsequent stability time points (Table 1).

The concentration of DMT fumarate was determined by HPLC at preparation and on the two subsequent stability occasions (Table 2). All results confirmed accurate preparation with no significant concentration changes on either Day 7 or Day 17. The only significant change over the course of the experiment was a drop in concentration following light stressing of the aliquot of the nominal pH 7 formulation. This was accompanied by a significant increase in observed degradants.

In terms of related substances, only peaks greater than 0.05% of the total peak area have been reported. The summarised related substances data are presented in Table 3, with individual values in Table 4 (7 days storage at 40° C.) and Table 5 (10 days storage at 40° C. with a further 7 days storage at 50° C.).

At preparation, no related substances peaks were present. On Day 7 only the pH 9 formulation contained a peak at a relative retention time of 1.11. With only minimal additional peaks observed following the 7 days elevated storage, the formulations were further stressed (with an increase in storage temperature over time) and on analysis after 17 days storage, additional peaks were present in several of the formulations with a clear trend visible with increasing numbers of peaks and peak area with increasing pH, ranging from no peaks (pH 4) to 3 peaks with a total peak area of 0.61% (pH 9). The nitrogen sparged formulation (pH 7) was significantly more robust than its unsparged equivalent confirming that oxidation is a degradation pathway. The light stressed formulation was the most degraded sample with a total related substances value of 1.68%.

TABLE 1 pH-stability measurement for SPL026 in Britton-Robinson buffer

| Nominal pH | Initial | Day 7[b] | Day 17[c] |
|---|---|---|---|
| 4.0 | 3.86 | 3.84 | 3.84 |
| 5.0 | 4.57 | 4.55 | 4.52 |
| 6.0 | 5.08 | 5.07 | 5.06 |
| 6.5 | 5.33 | 5.33 | 5.31 |
| 7.0 | 6.12 | 6.10 | 6.10 |
| 6.5 sparged $N_2$ | 6.12 | 6.18 | 6.09 |
| 7.0 UV Light | 6.07[a] | — | — |
| 7.5 | 6.60 | 6.58 | 6.59 |
| 8.0 | 6.87 | 6.86 | 6.84 |
| 9.0 | 7.71 | 7.72 | 7.70 |

[a] pH on completion of testing
[b] 7 days storage at 40° C.
[c] 10 days storage at 40° C. followed by 7 days at 50° C.

Table 1 shows that pH stability decreased with increasing pH, in particular for formulations with pH ≥7.

TABLE 2 pH-stability for SPL026 in Britton-Robinson buffer (assay)

| | Concentration (mg · mL$^{-1}$) | | | |
|---|---|---|---|---|
| Nominal pH | Initial | Day 7[b] | Day 17[c] | Light |
| 4.0 | 2.47 | 2.57 | 2.52 | — |
| 5.0 | 2.50 | 2.48 | 2.52 | — |
| 6.0 | 2.51 | 2.56 | 2.48 | — |
| 6.5 | 2.49 | 2.59 | 2.51 | — |
| 7.0 | 2.54 | 2.54 | 2.45 | — |
| 7.0 sparged $N_2$ | 2.54 | 2.54 | 2.51 | — |
| 7.0 UV Light | 2.54 | — | — | 2.26[a] |
| 7.5 | 2.50 | 2.55 | 2.46 | — |
| 8.0 | 2.49 | 2.49 | 2.42 | — |
| 9.0 | 2.47 | 2.41 | 2.46 | — |

[a] concentration on completion of light stressing (200 watt hours UVA, 0.6 million luxhours). This sample was an aliquot of the pH 7 solution
[b] 7 days storage at 40° C.
[c] 10 days storage at 40° C. followed by 7 days at 50° C.

It can be seen from Table 2 that the concentration of DMT fumarate in the solutions having a nominal pH ≥7 decreased over 17 days.

TABLE 3 pH stability total related substances assay for SPL026 in Britton-Robinson buffer

| | Total related substances (%) | | | |
|---|---|---|---|---|
| Nominal pH | Initial | Day 7[b] | Day 17[c] | Light |
| 4.0 | ND | ND | ND | — |
| 5.0 | ND | ND | 0.07 | — |
| 6.0 | ND | ND | 0.09 | — |
| 6.5 | ND | ND | 0.10 | — |
| 7.0 | ND | ND | 0.26 | — |
| 7.0 sparged $N_2$ | ND | ND | 0.05 | — |
| 7.0 UV Light | ND | — | — | 1.68[a] |
| 7.5 | ND | ND | 0.42 | — |
| 8.0 | ND | ND | 0.58 | — |
| 9.0 | ND | 0.10 | 0.61 | — |

ND—<0.02 area of total peak area
[a] % related substances on completion of light stressing (200 watt hours UVA, 0.6 million luxhours). This sample was an aliquot of the pH 7 solution
[b] 7 days storage at 40° C.
[c] 10 days storage at 40° C. followed by 7 days at 50° C.

Table 3 clearly shows that the amount of related substances increased with increasing pH, indicating decreased stability.

TABLE 4 pH stability individual related substances assay for SPL026 in Britton-Robinson buffer, 7 days storage at 40° C.

| | | Relative retention time and percentage area of total peak area (peaks > 0.05% of total peak area) | | | | | | | | | | | | | | |
|---|---|---|---|---|---|---|---|---|---|---|---|---|---|---|---|---|
| Nominal pH | Day[a] | 0.54 | 0.62 | 0.64 | 0.73 | 0.74 | 0.77 | 0.80 | 0.81 | 0.91 | 0.95 | 1.06 | 1.10 | 1.11 | 1.17 | 1.20 | 1.56 |
| 4 | 7 | — | — | — | — | — | — | — | — | — | — | — | — | — | — | — | — |
| 5 | 7 | — | — | — | — | — | — | — | — | — | — | — | — | — | — | — | — |
| 6 | 7 | — | — | — | — | — | — | — | — | — | — | — | — | — | — | — | — |
| 6.5 | 7 | — | — | — | — | — | — | — | — | — | — | — | — | — | — | — | — |
| 6.5 with $N_2$[a] | 7 | — | — | — | — | — | — | — | — | — | — | — | — | — | — | — | — |
| 7 UV light[b] | n/a[c] | 0.05 | 0.17 | 0.54 | 0.23 | 0.15 | 0.06 | 0 07 | — | — | — | — | — | — | 0.18 | 0.13 | 0.10 |
| 7 | 7 | — | — | — | — | — | — | — | — | — | — | — | — | — | — | — | — |
| 7.5 | 7 | — | — | — | — | — | — | — | — | — | — | — | — | — | — | — | — |
| 8 | 7 | — | — | — | — | — | — | — | — | — | — | — | — | — | — | — | — |
| 9 | 7 | — | — | — | — | — | — | — | — | — | — | — | — | — | — | — | — |

[a] Sparged with nitrogen
[b] UV light exposure (200 watt hours UVA, 0.6 million luxhours)
[c] Subsample of the pH 7 formulation

TABLE 5 pH stability individual related substances assay for SPL026 in Britton-Robinson buffer, 10 days storage at 40° C., 7 days storage at 50° C.

Relative retention time and percentage area of total peak area (peaks > 0.05% of total peak area)

| Nominal pH | Day[a] | 0.54 | 0.62 | 0.64 | 0.73 | 0.74 | 0.77 | 0.30 | 0.81 | 0.91 | 0.95 | 1.06 | 1.10 | 1.11 | 1.17 | 1.20 | 1.56 |
|---|---|---|---|---|---|---|---|---|---|---|---|---|---|---|---|---|---|
| 4 | 17 | — | — | — | — | — | — | — | — | — | — | — | — | — | — | — | — |
| 5 | 17 | — | — | — | — | — | — | — | — | — | — | — | — | — | — | — | 0.07 |
| 6 | 17 | — | — | — | — | — | — | — | — | — | — | — | — | — | — | — | 0.09 |
| 6.5 | 17 | — | — | — | — | — | — | — | — | — | — | — | — | — | — | — | 0.10 |
| 6.5 with N$_2$[a] | 17 | — | — | — | — | — | — | — | — | — | — | — | — | — | — | — | 0.05 |
| 7 | 17 | — | — | — | 0.09 | — | — | — | — | 0.05 | — | — | — | — | — | — | 0.12 |
| 7.5 | 17 | — | — | — | 0.14 | — | — | — | — | 0.07 | — | — | — | 0.12 | — | — | 0.09 |
| 8 | 17 | — | — | — | 0.15 | — | — | — | — | 0.09 | 0.05 | — | — | 0.22 | — | — | 0.07 |
| 9 | 17 | — | — | — | 0.12 | — | — | — | — | 0.11 | — | — | — | 0.12 | — | — | 0.38 |

[a]Sparged with nitrogen

Under accelerated conditions, total amounts of related substances at 17 days were found to increase for formulations having pH 7 or greater.

The data presented in Tables 1-5 above clearly show that stability of the tested formulations decreases with increasing pH. In particular, it was found that stability is improved for formulations that have a pH less than 7.

As described above, when developing formulations for injection, it is typical to match the pH of the formulation with those of the patient's blood serum. Human blood serum has a pH of about 7.4. Consequently, the obvious formulation of salts of optionally substituted dimethyltryptamine compounds is one with a pH of about 7.4. A greater stability of formulations of such salts prepared at pH values of less than 7.0 was unexpected.

Formulation Preparation

Details of each individual example formulation are presented in the table below. Each formulation may be prepared by a process analogous to the example below.

An aliquot of each formulation may be taken for assay/related substances and osmolality check. The remainder of each formulation is filtered (filter size 0.2 μm) into a clear glass multi-dose vial, sparged with nitrogen, and capped.

Preparation of Example Formulation (25 mg/mL, pH 5.5)

1) Weigh the required amount of drug substance into a suitable container (glass weigh boat). Ensure that mass of drug substance taken includes correction for salt and purity.
2) Carefully transfer the weighed drug substance into a beaker. Rinse out the weighing container with water for injection (WFI) ensuring no solids remain. Add further WFI to the drug substance up to ¾ of the required total volume and magnetically stir to dissolve.
3) Make to volume in a suitable container and lastly check the pH is pH 5.5 (±0.1) and adjust if required.
4) The drug product solution is clear with a very slight hint of a beige colour (using N,N-dimethyltryptamine fumarate). This colour is removed on filtration (step 6) to leave a colourless solution filtration.
5) Bubble nitrogen through the formulation until the measured dissolved oxygen content is below 5 ppm, preferably below 2 ppm.
6) Syringe filter the solution into a suitable glass multi-does vial, suitably either 0.22 μm or 0.2 μm into a glass multi-dose vial.

Example formulations, comprising a co-solvent, surfactant, buffer, pH adjuster or tonicity agent, or other excipient.

| | | Use |
|---|---|---|
| 1 | 10 to 150 mg/ml DS (as free base) Up to 0.08% w/v ethanol | Co-solvent |
| 2 | 10 to 150 mg/ml DS (as free base) Up to 25% w/w Propylene glycol | Co-solvent |
| 3 | 10 to 150 mg/ml DS (as free base) Up to 0.02% w/w benzalkonium chloride | Surfactant/preservative |
| 4 | 10 to 150 mg/ml DS (as free base) Up to 0.42% w/v citric acid monohydrate | Buffer, antioxidant |
| 5 | 10 to 150 mg/ml DS (as free base) Up to 5% w/w glycerin | Humectant |
| 6 | 10 to 150 mg/ml DS (as free base) Up to 0.9% w/v sodium chloride | Tonicity agent |
| 7 | 10 to 150 mg/ml DS (as free base) Hydrochloric acid Sodium hydroxide | pH adjuster or Tonicity agent Base agent |
| 8 | 10 to 150 mg/ml DS (as free base) Up to 0.3% w/w sodium metabisulphite | Antioxidant |
| 9 | 10 to 150 mg/ml DS (as free base) Up to 24 mg trisodium citrate dihydrate | Buffer |
| 10 | 10 to 150 mg/ml DS (as free base) Up to 0.05% w/v edetate disodium | Chelating agent |

The formulations of the invention may comprise one or more of the excipients listed above.

'DS' refers to the optionally substituted dimethyltryptamine compound for use in the formulations of the present invention.

Example 9: N,N-Dimethyltryptamine pH-solubility pH solubility samples were prepared in 0.5M Britton Robinson (BR) buffer. Prior to adding N,N-dimethyltryptamine, a quantity of NaOH was added to the BR buffer as required to ensure the required pH. The total volume of BR buffer plus required amount of NaOH was 5 ml for each pH tested (pH 4, 5, 6, 7, 8, 9 & 10). 150 mg of N,N-dimethyltryptamine was then added and the pH checked before shaking overnight at ambient temperature.

Figure 3:
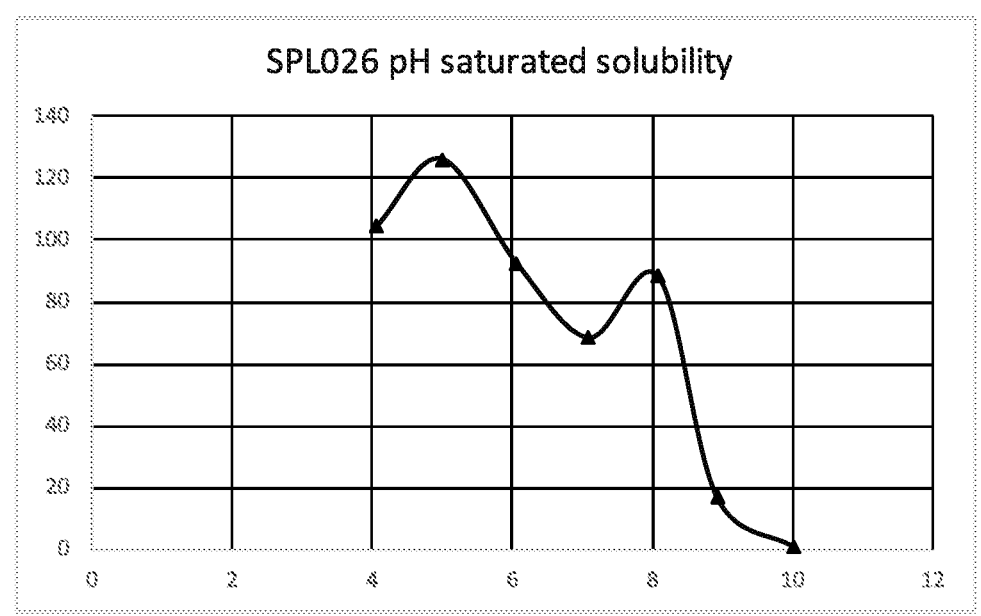
FIG. 3 shows the pH-solubility curve for N,N-dimethyltryptamine from pH 4 to pH 10.

The solubility of N,N-Dimethyltryptamine was determined at varying pH at 25° C. as shown in the following table and in FIG. 3:

| pH | Real data (mg/mL) |
|---|---|
| 4.05 | 104.6 |
| 4.98 | 126.3 |
| 6.05 | 92.6 |
| 7.08 | 68.6 |
| 8.07 | 88.4 |
| 8.91 | 17.1 |
| 10.01 | 1.14 |

Solubility of 90 mg/mL or greater was observed at a pH between about 4 and about 6, with the highest solubility observed at a pH of around 5.

A solubility headspace of around 2-3 fold is ideally allowed to reduce the risk of precipitation on long term storage and/or temporary storage at temperatures below the recommended storage temperature. These data support a 100 mg/2.5 mL (40 mg/ml) dose at a pH of from about 5 to about 6.5, while achieving the desirable 2-3 fold solubility headspace at 25° C.

Example 10: Example Formulations

Example formulations of the invention are as set out in the following table.

| Component | Unit Quantity (per mL) | Function |
|---|---|---|
| DMT fumarate or deuterated analogue | 25 mg (as free base) | Active ingredient |
| Trisodium citrate dihydrate | 1.47 mg | Buffer |
| Sodium Hydroxide | q.s. to pH 6 | Base agent |
| Hydrochloric acid | q.s. to pH 6 | pH adjuster |
| Water for injection | q.s. to 1.0 mL | Solvent |
| Nitrogen | q.s. | antioxidant | q.s. means a sufficient quantity

Example 11: Stability

Formulations of DMT fumarate (Example 2), and of deuterated DMT fumarate (Example 2), prepared in accordance with Example 10, were assessed for stability after storage for 3 months at 2-8° C., at 25° C./60% RH and at 40° C./75% RH.

For the formulation comprising DMT fumarate, no related substances above the limit of quantitation (≥0.05% w/w) were observed at T=0, or after 3 months storage at 2-8° C. and at 25° C./60% RH. After 3 months storage at 40° C./75% RH, a total of 0.35% w/w related substances were observed. For the formulation comprising deuterated DMT fumarate, no related substances above the limit of quantitation (≥0.05% w/w) were observed at T=0, or after 3 months storage at 2-8° C. and at 25° C./60% RH. After 3 months storage at 40° C./75% RH, a total of 0.33% w/w related substances were observed.

These data indicate good stability for the formulations of the current invention, with a low amount of related substances only observed under stressed conditions of 40° C./75% RH. The invention may be further understood with reference to the following non-limiting clauses:

[1]. A pharmaceutical formulation suitable for intramuscular injection and/or nebuliser inhalation, comprising a salt of an optionally substituted dimethyltryptamine compound; and water; wherein the formulation has a pH of from about 5 to about 6, a concentration of about 10 mg/ml as freebase or greater, and an osmolality of from about 250 to about 350 mOsm/Kg.

[2]. A pharmaceutical formulation suitable for intramuscular injection and/or nebuliser inhalation, comprising a salt of an optionally substituted dimethyltryptamine compound; and water; wherein the formulation has a pH of from about 5 to about 6.5, a concentration of about 10 mg/ml as freebase or greater, and an osmolality of from about 250 to about 350 mOsm/Kg.

[3]. A pharmaceutical formulation suitable for intramuscular injection and/or nebuliser inhalation, comprising a salt of an optionally substituted dimethyltryptamine compound; a base agent, water, and optionally a buffer which is separate to the salt; wherein the formulation has a pH of from about 5 to about 6, a concentration of about 10 mg/ml as freebase or greater, and an osmolality of from about 250 to about 350 mOsm/Kg; and wherein the formulation comprises a dose of the optionally substituted dimethyltryptamine compound within a volume for injection or inhalation of 5 ml or less.

[4]. A pharmaceutical formulation suitable for intramuscular injection and/or nebuliser inhalation, comprising a salt of an optionally substituted dimethyltryptamine compound; a base agent, water, and optionally a buffer which is separate to the salt; wherein the formulation has a pH of from about 5 to about 6.5, a concentration of about 10 mg/ml as freebase or greater, and an osmolality of from about 250 to about 350 mOsm/Kg; and wherein the formulation comprises a dose of the optionally substituted dimethyltryptamine compound within a volume for injection or inhalation of 5 ml or less.

[5]. The formulation of any preceding clause, wherein formulation comprises an effective dose of an optionally substituted dimethyltryptamine compound for use in psychedelic assisted therapy within a volume of 5 ml or less.

[6]. The formulation of any preceding clause, wherein the volume is 3 ml or less.

[7]. The formulation of any preceding clause, wherein the volume is 2.5 ml or less.

[8]. The formulation of any preceding clause, wherein the formulation has an osmolality of from about 275 to about 325 mOsm/Kg.

[9]. The formulation of any preceding clause, wherein the salt of the optionally substituted dimethyltryptamine compound comprises a Brønsted acid having a pKa of from about 3 to about 5 and a compound of Formula I:

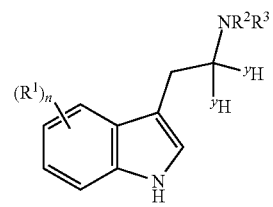

Formula I wherein:

$R^1$ is independently selected from —$R^4$, —OH, —$OR^4$, —$O(CO)R^4$, monohydrogen phosphate, —F, —Cl, —Br and —I;

n is selected from 0, 1, 2, 3 or 4;

$R^2$ is $C(^xH)_3$;

$R^3$ is $C(^xH)_3$;

each $R^4$ is independently selected from $C_1$-$C_4$alkyl; and
each $^xH$ and $^yH$ is independently selected from protium or deuterium.

[10]. The formulation of any preceding clause, wherein the salt of the optionally substituted dimethyltryptamine compound comprises a Brønsted acid having a pKa of from about 3 to about 5 and a compound of Formula IA or of Formula IB:

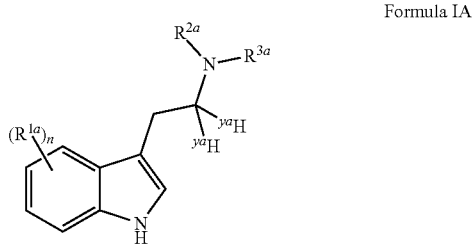

Formula IA wherein:
$R^{1a}$ is independently selected from —$R^{4a}$, —OH, —O$R^{4a}$, —O(CO)$R^{4a}$, monohydrogen phosphate, —F, —Cl, —Br and —I;
n is selected from 0, 1, 2, 3 or 4;
$R^{2a}$ is C($^{xa}$H)$_3$;
$R^{3a}$ is C($^{xa}$H)$_3$;
each $R^{4a}$ is independently selected from $C_1$-$C_4$alkyl; and
each $^{xa}H$ and $^{ya}H$ is independently selected from protium or deuterium;

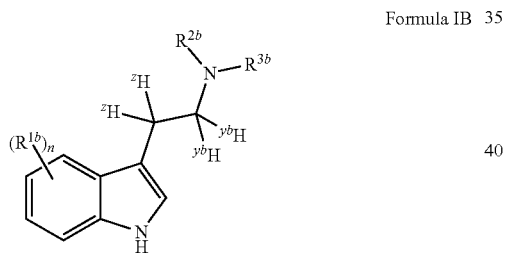

Formula IB wherein:
$R^{1b}$ is independently selected from —$R^{4b}$, —OH, —O$R^{4b}$, —O(CO)$R^{4b}$, monohydrogen phosphate, —F, —Cl, —Br and —I;
n is selected from 0, 1, 2, 3 or 4;
$R^{2b}$ is C($^{xb}$H)$_3$;
$R^{3b}$ is C($^{xb}$H)$_3$;
each $R^{4b}$ is independently selected from $C_1$-$C_4$alkyl; and
each $^{xb}H$, $^{yb}H$ and $^zH$ is independently selected from protium or deuterium.

[11]. The formulation of clause 9 or clause 10, wherein the salt of the optionally substituted dimethyltryptamine compound comprises (i) a compound of Formula I, wherein n is 0; or n is 1 and $R^1$ is in the 4- or 5-position; or (ii) a compound of Formula IA, wherein n is 0; or n is 1 and $R^{1a}$ is in the 4- or 5-position, or (iii) a compound of Formula IB, wherein n is 0; or n is 1 and $R^{1b}$ is in the 4- or 5-position.

[12]. The formulation of any one of clauses 9 to 11, wherein the salt of the optionally substituted dimethyltryptamine compound comprises (i) a compound of Formula I, wherein each $R^1$ is independently selected from —OH, —OMe, —OCD$_3$, —OAc, —O(CO)Me, and monohydrogen phosphate; or (ii) a compound of Formula IA, wherein each $R^{1a}$ is independently selected from —OH, —OMe, —OCD$_3$, —OAc, —O(CO)Me, and monohydrogen phosphate, or (iii) a compound of Formula IB, wherein each $R^{1b}$ is independently selected from —OH, —OMe, —OCD$_3$, —OAc, —O(CO)Me, and monohydrogen phosphate.

[13]. The formulation of any one any of clauses 9 to 12, wherein the salt of the optionally substituted dimethyltryptamine compound comprises (i) a compound of Formula I, wherein $R^2$ is CD$_3$ and $R^3$ is CD$_3$; or (ii) a compound of Formula IA, wherein $R^{2a}$ is CD$_3$ and $R^{3a}$ is CD$_3$, or (iii) a compound of Formula IB, wherein $R^{2b}$ is CD$_3$ and $R^{3b}$ is CD$_3$.

[14]. The formulation of any one any of clauses 9 to 12, wherein the salt of the optionally substituted dimethyltryptamine compound comprises (i) a compound of Formula I, wherein $R^2$ is CH$_3$ and $R^3$ is CH$_3$; or (ii) a compound of Formula IA, wherein $R^{2a}$ is CH$_3$ and $R^{3a}$ is CH$_3$, or (iii) a compound of Formula IB, wherein $R^{2b}$ is CH$_3$ and $R^{3b}$ is CH$_3$.

[15]. The formulation of any one any of clauses 9 to 12, wherein the salt of the optionally substituted dimethyltryptamine compound comprises (i) a compound of Formula I, wherein $R^2$ is CH$_3$ and $R^3$ is CD$_3$; or (ii) a compound of Formula IA, wherein $R^{2a}$ is CH$_3$ and $R^{3a}$ is CD$_3$, or (iii) a compound of Formula IB, wherein $R^{2b}$ is CH$_3$ and $R^{3b}$ is CD$_3$.

[16]. The formulation of any one of clauses 9 to 12, wherein the salt of the optionally substituted dimethyltryptamine compound comprises (i) a compound of Formula I, wherein each $^xH$ is D; or a compound of Formula IA, wherein each $^{xa}H$ is D; or (iii) a compound of Formula IB, wherein each $^{xb}H$ is D.

[17]. The formulation of any one of clauses 9 to 16, wherein the salt of the optionally substituted dimethyltryptamine compound comprises (i) a compound of Formula I, wherein both $^yH$ are D; or (ii) a compound of Formula IA, wherein both $^{ya}H$ are D; or (iii) a compound of Formula IB, wherein both $^{yb}H$ are D.

[18]. The formulation of any one of clauses 9 to 16, wherein the salt of the optionally substituted dimethyltryptamine compound comprises (i) a compound of Formula I, wherein one $^yH$ is H and one $^yH$ is D; or (ii) a compound of Formula IA, wherein one $^{ya}H$ is H and one $^{ya}H$ is D; or (iii) a compound of Formula IB, wherein one $^{yb}H$ is H and one $^{yb}H$ is D.

[19]. The formulation of any one of clauses 9 to 16, wherein the salt of the optionally substituted dimethyltryptamine compound comprises (i) a compound of Formula I, wherein both $^yH$ are H; or (ii) a compound of Formula IA, wherein both $^{ya}H$ are H; or (iii) a compound of Formula IB, wherein both $^{yb}H$ are H.

[20]. The formulation of any one of clauses 10 to 19, wherein the salt of the optionally substituted dimethyltryptamine compound comprises a compound of Formula IB, wherein both $^zH$ are D.

[21]. The formulation of any one of clauses 10 to 19, wherein the salt of the optionally substituted dimethyltryptamine compound comprises a compound of Formula IB, wherein both $^zH$ are H.

[22]. The formulation of any one of clauses 10 to 19, wherein the salt of the optionally substituted dimethyltryptamine compound comprises a compound of Formula IB, wherein one $^zH$ is H and one $^zH$ is D.

[23]. The formulation of any one of clauses 9 to 11 and 13 to 22 wherein n is 0.

[24]. The formulation of any one of clauses 9 to 22 wherein n is 1 and $R^1$ or $R^{1a}$ or $R^{1b}$ is 4-acetoxy.

[25]. The formulation of any one of clauses 9 to 22 wherein n is 1 and $R^1$ or $R^{1a}$ or $R^{1b}$ is 5-methoxy or trideutero-5-methoxy.

[26]. The formulation of any one of clauses 1 to 9, wherein the optionally substituted dimethyltryptamine compound is N,N-dimethyltryptamine.

[27]. The formulation of any one of clauses 1 to 25, wherein the optionally substituted dimethyltryptamine compound is selected from α,α-dideutero-N,N-dimethyltryptamine ($d_2$-DMT) α,α,β,β-tetradeutero-N,N-dimethyltryptamine ($d_4$-DMT), N,N-di(trideuteromethyl)tryptamine ($d_6$-DMT), α,α-dideutero-N,N-di(trideuteromethyl)tryptamine ($d_8$-DMT), α,α,β,β-tetradeutero-N,N-di(trideuteromethyl)tryptamine ($d_{10}$-DMT), 5-methoxy-α,α-dideutero-N,N-di(trideuteromethyl)tryptamine, α,α-dideutero-N,N-di(trideuteromethyl)tryptamine ($d_8$-DMT), α,α,β,β-tetradeutero-N,N-di(trideuteromethyl)tryptamine ($d_{10}$-DMT), 5-methoxy-N,N-di(trideuteromethyl)tryptamine, 5-methoxy-α,α-dideutero-N,N-di(trideuteromethyl)tryptamine, 5-methoxy-α,α,β,β-tetradeutero-N,N-di(trideuteromethyl)tryptamine and mixtures thereof

[28]. The formulation of any preceding clause, wherein the salt of the optionally substituted dimethyltryptamine compound is of an optionally substituted dimethyltryptamine compound and an acid selected from the group consisting of fumaric acid, tartaric acid, citric acid, acetic acid, lactic acid and gluconic acid.

[29]. The formulation of clause 28, wherein the acid is fumaric acid.

[30]. The formulation of any preceding clause comprising a drug substance which comprises the salt of the optionally substituted dimethyltryptamine compound at a purity of greater than or equal to 99% when measured by HPLC.

[31]. The formulation of any preceding clause, wherein the concentration of the optionally substituted dimethyltryptamine is from about 10 mg/mL to about 150 mg/mL (as the freebase equivalent).

[32]. The formulation of any preceding clause, wherein the concentration of the optionally substituted dimethyltryptamine is from about 15 mg/mL to about 70 mg/mL (as the freebase equivalent).

[33]. The formulation of any preceding clause, wherein the concentration of the optionally substituted dimethyltryptamine compound is from about 20 mg/mL to about 40 mg/mL (as the freebase equivalent).

[34]. The formulation of any preceding clause, wherein the concentration of the optionally substituted dimethyltryptamine is about 20 mg/mL or greater (as the freebase equivalent).

[35]. The formulation of any preceding clause, wherein the concentration of the optionally substituted dimethyltryptamine compound is about 25 mg/mL or greater (as the freebase equivalent).

[36]. The formulation of any preceding clause, wherein the formulation further comprises a buffer which is separate to the salt.

[37]. The formulation of clause 33, wherein the buffer comprises an acetate salt and acetic acid; or a citrate salt and citric acid; or a phosphate salt and phosphoric acid; or the buffer comprises an acetate salt, a citrate salt, or a phosphate salt.

[38]. The formulation of any preceding clause, wherein the base agent is sodium hydroxide or potassium hydroxide.

[39]. The formulation of any preceding clause, wherein the formulation further comprises a tonicity agent.

[40]. The formulation of any preceding clause, wherein the formulation consists essentially of the salt of the optionally substituted dimethyltryptamine compound, water, and the base agent, and optionally one or more agents selected from a tonicity agent, a buffer, a co-solvent, a preservative, and an antioxidant.

[41]. The formulation of any preceding clause, wherein the formulation consists essentially of the salt of the optionally substituted dimethyltryptamine compound, water, optionally the buffer and optionally the tonicity agent.

[42]. The formulation of any preceding clause, wherein the formulation consists essentially of the salt of the optionally substituted dimethyltryptamine compound, the base agent, water, optionally the buffer and optionally the tonicity agent.

[43]. The formulation of any one of clauses 1 to 32 and 39 to 42, wherein the formulation consists of the salt of the optionally substituted dimethyltryptamine compound, water, and optionally the tonicity agent.

[44]. The formulation of any one of clauses 3 to 32 and 39 to 42, wherein the formulation consists of the salt of the optionally substituted dimethyltryptamine compound, the base agent, water, and optionally the tonicity agent.

[45]. The formulation of any one of clauses 39 to 44, wherein the tonicity agent is sodium chloride or dextrose.

[46]. The formulation of any one of clauses 1 to 45, having an oxygen content of less than 5 ppm.

[47]. The formulation of any one of clauses 1 to 45, having an oxygen content of less than 2 ppm.

[48]. The formulation of any preceding clause, wherein the formulation has been sparged with an inert gas.

[49]. The formulation of any preceding clause, stored in a container having a volume of 5 ml or less.

[50]. The formulation of any preceding clause, stored in a container having a volume of 4 ml or less.

[51]. The formulation of any preceding clause, stored in a container having a volume of 3 ml or less.

[52]. The formulation of any preceding clause, stored in a container having a volume of 2 ml or less.

[53]. The formulation of any preceding clause, stored in a container having a volume of 1 ml or less.

[54]. The formulation of any preceding clause, stored in a container having a volume of 0.5 ml or less.

[55]. The formulation of any preceding clause, wherein the formulation further comprises a pH adjuster.

[56]. The formulation of clause 55, wherein the pH adjuster comprises hydrochloric acid.

[57]. The formulation of clause 56, comprising the salt of the optionally substituted dimethyltryptamine compound, the base agent, water, and a pH adjuster.

[58]. A kit suitable for preparing a formulation of any preceding clause, said kit comprising a salt of an optionally substituted dimethyltryptamine compound; optionally a tonicity agent; and optionally a buffer which is separate to the salt.

[59]. A kit suitable for preparing a formulation of any one of clauses 3 to 57, said kit comprising a salt of an optionally substituted dimethyltryptamine compound; optionally a tonicity agent; a base agent and optionally a buffer which is separate to the salt.

[60]. A method of preparing a pharmaceutical formulation as defined in any one of clauses 1 to 57, comprising contacting the salt of the optionally substituted dimethyltryptamine compound, water and optionally a buffer, and optionally a tonicity agent.

[61]. A method of preparing a pharmaceutical formulation as defined in any one of clauses 3 to 57, comprising contacting the salt of the optionally substituted dimethyltryptamine compound, water, a base agent and optionally a buffer which is separate to the salt, and optionally a tonicity agent.

[62]. The method of clause 60 or clause 61 wherein an aqueous solution of the buffer is contacted with the salt of the optionally substituted dimethyltryptamine compound, wherein the aqueous solution has a pH as defined in clause 1 or 2.

[63]. The method of any one of clauses 60 to 62, wherein the method comprises contacting the optionally substituted dimethyltryptamine compound with a buffer, water and optionally a tonicity agent.

[64]. The method of any one of clauses 60 to 63, further comprising adjusting the pH of the formulation.

[65]. The method of clause 64 wherein the pH is adjusted with a base agent, which is preferably sodium hydroxide or potassium hydroxide.

[66]. The method of clause 64 or clause 65, which further comprises adjusting the pH with a pH adjuster, which is preferably hydrochloric acid.

[67]. The method of any one of clauses 60 to 66 further comprising sparging the formulation with an inert gas.

[68]. A formulation as defined in any one of clauses 1 to 57 or the kit of clause 58 or clause 59 for use as a medicament, or in combination with psychotherapy (i.e. in pharmacological-assisted psychotherapy).

[69]. A formulation as defined in any one of clauses 1 to 57 or the kit of clause 58 or clause 59 for use in a method of treating a psychiatric or neurological disorder in a patient.

[70]. The formulation for the use of clause 69 wherein the psychiatric or neurological disorder is selected from the group consisting of (i) an obsessive compulsive disorder, (ii) a depressive disorder, (iii) an anxiety disorder, (iv) substance abuse and gambling disorders, and (v) an avolition disorder.

[71]. A method of treating a psychiatric or neurological disorder comprising administering to a patient in need thereof a formulation as defined in any one of clauses 1 to 57.

[72]. The method of clause 71, wherein the psychiatric or neurological disorder is as defined in clause 70.

[73]. The method of clause 71, wherein the formulation as defined in any one of clauses 1 to 57 is administered in combination with psychotherapy.

[74]. The formulation according to any one of clauses 1 to 57, the formulation for use according to any one of clauses 68 to 70, or the method according to any one of clauses 71 to 73, wherein the dose of the optionally substituted dimethyltryptamine compound is in the range of from about 5 to about 250 mg.

[75]. The formulation according to any one of clauses 1 to 57, the formulation for use according to any one of clauses 68 to 70, or the method according to any one of clauses 71 to 73, wherein the dose of the optionally substituted dimethyltryptamine compound is in the range of from about 10 to about 150 mg.

[76]. The formulation according to any one of clauses 1 to 57, the formulation for use according to any one of clauses 68 to 70, or the method according to any one of clauses 71 to 73, wherein the dose of the optionally substituted dimethyltryptamine compound is in the range of from about 10 to about 100 mg.

[77]. The formulation according to any one of clauses 1 to 57, the formulation for use according to any one of clauses 68 to 70, or the method according to any one of clauses 71 to 73, wherein the dose of the optionally substituted dimethyltryptamine compound is in the range of from about 20 to about 70 mg.

[78]. The formulation according to any one of clauses 1 to 57, the formulation for use according to any one of clauses 68 to 70, or the method according to any one of clauses 71 to 73, wherein the dose of the optionally substituted dimethyltryptamine compound is in the range of from about 20 to about 50 mg.

[79]. The formulation according to any one of clauses 1 to 57, the formulation for use according to any one of clauses 68 to 70, or the method according to any one of clauses 71 to 73, wherein the formulation comprises:

a) the salt of an optionally substituted dimethyltryptamine compound selected from $\alpha,\alpha$-dideutero-N,N-dimethyltryptamine ($d_2$-DMT) $\alpha,\alpha,\beta,\beta$-tetradeutero-N,N-dimethyltryptamine ($d_4$-DMT), N,N-di(trideuteromethyl)tryptamine ($d_6$-DMT), $\alpha,\alpha$-dideutero-N,N-di(trideuteromethyl)tryptamine ($d_8$-DMT), $\alpha,\alpha,\beta,\beta$-tetradeutero-N,N-di(trideuteromethyl)tryptamine ($d_{10}$-DMT), 5-methoxy-$\alpha,\alpha$-dideutero-N,N-di(trideuteromethyl)tryptamine, 5-methoxy-N,N-di(trideuteromethyl)tryptamine and 5-methoxy-$\alpha,\alpha$-dideutero-N,N-di(trideuteromethyl)tryptamine, and mixtures thereof, and an acid selected from the group consisting of fumaric acid, tartaric acid, citric acid, acetic acid, lactic acid and gluconic acid;

b) a base agent selected from sodium hydroxide and potassium hydroxide;

c) water;

d) optionally a buffer which is separate from the salt and which comprises an acetate salt and acetic acid; or a citrate salt and citric acid; or a phosphate salt and phosphoric acid; or which comprises an acetate salt, a citrate salt, or a phosphate salt;

e) optionally a pH adjuster which is hydrochloric acid.

wherein the formulation has a pH of from about 5 to about 6.5, or a pH of from about 5 to about 6, a concentration of from about 15 mg/mL to about 70 mg/mL (as the freebase equivalent), and an osmolality of from about 250 to about 350 mOsm/Kg; and wherein the formulation comprises a dose of the optionally substituted dimethyltryptamine compound in the range of from about 10 mg to about 100 mg within a volume of 5 ml or less.

The invention claimed is:

1. A pharmaceutical formulation suitable for intramuscular injection, comprising a salt of a compound of Formula IB:

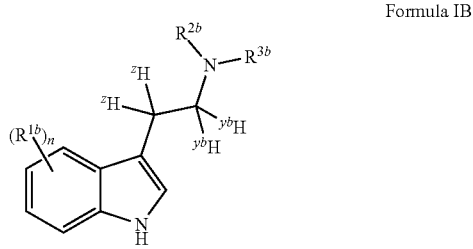

Formula IB wherein:
n is 0;
$R^{1b}$ is independently selected from —$R^{4b}$, —OH, —$OR^{4b}$, —$O(CO)R^{4b}$, monohydrogen phosphate, —F, —Cl, —Br or —I;
$R^{2b}$ is $C(^{xb}H)_3$;
$R^{3b}$ is $C(^{xb}H)_3$;
each $R^{4b}$ is independently selected from $C_1$-$C_4$alkyl; and each $^{xb}H$, $^{yb}H$ and $^{z}H$ is independently selected from protium or deuterium;
and a Brønsted acid having a pKa of from about 3 to about 5;
a base agent, water, and optionally a buffer which is separate to the salt;
wherein the formulation has a pH of from about 5 to about 6.5, a concentration of the compound of Formula IB of about 10 mg/ml or greater as the freebase equivalent, and an osmolality of from about 250 to about 350 mOsm/Kg; and wherein the formulation comprises a dose of the compound of Formula IB within a volume of 5 ml or less.

2. The formulation of claim 1, wherein the formulation has a pH of from about 5 to about 6.

3. The formulation of claim 1, wherein the formulation comprises a dose of the compound of Formula IB within a volume of 3 ml or less.

4. The formulation of claim 1, wherein $R^{2b}$ is $CD_3$ and $R^{3b}$ is $CD_3$; and/or wherein each $^{yb}H$ is D.

5. The formulation of claim 1, wherein the compound of Formula IB is N,N-dimethyltryptamine.

6. The formulation of claim 1, wherein the compound of Formula IB is selected from the group consisting of α,α-dideutero-N,N-dimethyltryptamine, α,α-dideutero-N,N-di(trideuteromethyl)tryptamine, α,α,β,β-tetradeutero-N,N-dimethyltryptamine, and α,α,β,β-tetradeutero-N,N-di(trideuteromethyl)tryptamine.

7. The formulation of claim 1, wherein the Brønsted acid is selected from the group consisting of fumaric acid, tartaric acid, citric acid, acetic acid, lactic acid and gluconic acid.

8. The formulation of claim 1, wherein the concentration of the compound of Formula IB is from about 20 mg/mL to about 40 mg/mL (as the freebase equivalent).

9. The formulation of claim 1, wherein the formulation comprises the buffer which is separate to the salt, optionally wherein the buffer comprises an acetate salt and acetic acid; or a citrate salt and citric acid; or a phosphate salt and phosphoric acid; or the buffer comprises an acetate salt, a citrate salt, or a phosphate salt.

10. The formulation of claim 1, wherein the formulation further comprises a tonicity agent and/or a pH adjuster.

11. The formulation of claim 1, wherein the formulation consists of the salt of the compound of Formula IB, water, the base agent and optionally the buffer and/or a tonicity agent and/or pH adjuster.

12. The formulation of claim 1, having an oxygen content of less than 5 ppm, or less than 2 ppm.

13. The formulation of claim 1, comprising the salt of the compound of Formula IB, the base agent, water, the buffer which is separate to the salt, and a tonicity agent or pH adjuster.

14. The formulation of claim 13, comprising a salt of the compound of Formula IB; the base agent which is selected from potassium hydroxide or sodium hydroxide; water; the buffer which is a citrate salt; and the tonicity agent or pH adjuster which is an acid.

15. A kit suitable for preparing the formulation of claim 1, said kit comprising the salt of the compound of Formula IB; optionally a tonicity agent and/or a pH adjuster; the base agent and optionally the buffer which is separate to the salt.

16. A lyophilised powder formulation comprising the formulation according to claim 1 which has been lyophilised.

17. The formulation of claim 1, wherein the concentration of the compound of Formula IB is about 25 mg/mL (as the freebase equivalent).

18. The formulation of claim 1, wherein the compound of Formula IB is a deuterated N,N-dimethyltryptamine.

19. The formulation of claim 18, wherein the deuterated N,N-dimethyltryptamine is selected from the group consisting of α,α-dideutero-N,N-dimethyltryptamine, α,α-dideutero-N,N-di(trideuteromethyl)tryptamine, α,α,β,β-tetradeutero-N,N-dimethyltryptamine, and α,α,β,β-tetradeutero-N,N-di(trideuteromethyl)tryptamine.

20. A pharmaceutical formulation suitable for intramuscular injection, comprising:
a fumarate salt of deuterated N,N-dimethyltryptamine selected from the group consisting of α,α-dideutero-N,N-dimethyltryptamine, α,α-dideutero-N,N-di(trideuteromethyl)tryptamine, α,α,β,β-tetradeutero-N,N-dimethyltryptamine, and α,α,β,β-tetradeutero-N,N-di(trideuteromethyl)tryptamine;
a base agent selected from potassium hydroxide and sodium hydroxide;
water; and
a buffer which comprises an acetate salt, a citrate salt, or a phosphate salt;
wherein the formulation has a pH of from about 5 to about 6.5, a concentration of the deuterated N,N-dimethyltryptamine from about 20 mg/mL to about 40 mg/mL as the freebase equivalent, and an osmolality of from about 250 to about 350 mOsm/Kg; and
wherein the formulation comprises a dose of the deuterated N,N-dimethyltryptamine within a volume of 5 ml or less.

21. A formulation according to claim 20, comprising a fumarate salt of α,α,β,β-tetradeutero-N,N-di(trideuteromethyl)tryptamine.

* * * * *